(12) United States Patent
Jeys et al.

(10) Patent No.: US 7,920,261 B2
(45) Date of Patent: Apr. 5, 2011

(54) METHOD AND APPARATUS FOR DETECTING AND DISCRIMINATING PARTICLES IN A FLUID

(75) Inventors: Thomas H. Jeys, Lexington, MA (US); Antonio Sanchez-Rubio, Lexington, MA (US); Richard J. Molnar, Harvard, MA (US); Robert K. Reich, Tyngsborough, MA (US); Jinendra K. Ranka, Westford, MA (US); David L. Spears, Acton, MA (US); Richard M. Osgood, III, Winchester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 583 days.

(21) Appl. No.: 12/029,300

(22) Filed: Feb. 11, 2008

(65) Prior Publication Data
US 2010/0053614 A1 Mar. 4, 2010

(51) Int. Cl.
*G01N 21/00* (2006.01)
(52) U.S. Cl. .......................................... 356/338; 356/73
(58) Field of Classification Search .......... 356/335–343, 356/73
See application file for complete search history.

(56) References Cited

U.S. PATENT DOCUMENTS

| | | | |
|---|---|---|---|
| 4,643,566 A | 2/1987 | Ohe et al. | |
| 5,282,151 A | 1/1994 | Knollenberg | |
| 5,793,478 A | 8/1998 | Rader et al. | |
| 5,883,707 A | 3/1999 | Arndt et al. | |
| 5,920,388 A | 7/1999 | Sandberg et al. | |
| 6,867,410 B2 | 3/2005 | Sasaki et al. | |
| 7,471,393 B2 | 12/2008 | Trainer | |
| 7,772,579 B2 * | 8/2010 | Herzog et al. | 250/574 |
| 7,821,636 B2 * | 10/2010 | Jeys et al. | 356/342 |
| 2001/0040214 A1 | 11/2001 | Friedman et al. | |
| 2002/0122167 A1 | 9/2002 | Riley et al. | |

(Continued)

FOREIGN PATENT DOCUMENTS

DE    39 31 119 C1    4/1991

(Continued)

OTHER PUBLICATIONS

R. M. Huffaker, "Laser Doppler detection systems for gas velocity measurement," Appl. Opt. vol. 9, No. 1, 1026-1039 (Jan. 1970).

(Continued)

*Primary Examiner* — Hoa Q Pham
(74) *Attorney, Agent, or Firm* — Hamilton, Brook, Smith & Reynolds, P.C.

(57) ABSTRACT

A particle detection system that images and detects particles in a fluid flow stream through use of detector array(s) is described. The detection system may include light source arrays that may selectively illuminate a particle in a fluid stream. The detection system may also include a detector array employing smart binning to read the measured signals. The smart binning of the detector array may be achieved through knowledge of an exact particle location provided by a position sensitive detector. The detector array(s) may be low cost based on intelligence built into the system. This particle detection system may be particularly useful for detection and discrimination of different particle types since the read-out of the particle signals can be accomplished with low noise and can be flexible enough to optimize the read out measurements for each particle. The particle detection system may be used, for example, in early warning contamination detection systems and manufacturing processes.

32 Claims, 17 Drawing Sheets

U.S. PATENT DOCUMENTS

| | | | |
|---|---|---|---|
| 2005/0122522 A1* | 6/2005 | Padmanabhan et al. | 356/436 |
| 2006/0066837 A1 | 3/2006 | Ortyn et al. | |
| 2006/0204071 A1 | 9/2006 | Ortyn et al. | |
| 2008/0030716 A1 | 2/2008 | Jeys et al. | |
| 2008/0068605 A1 | 3/2008 | Herzog et al. | |
| 2009/0219530 A1* | 9/2009 | Mitchell et al. | 356/336 |

FOREIGN PATENT DOCUMENTS

| | | |
|---|---|---|
| DE | 198 34 583 C1 | 12/1999 |
| DE | 199 26 494 A1 | 12/2000 |
| DE | 199 54 702 A1 | 5/2001 |
| EP | 0 467 127 A2 | 1/1992 |
| JP | 61-29737 | 10/1986 |
| WO | WO 98/41876 | 9/1998 |
| WO | WO 01/79861 A1 | 10/2001 |
| WO | WO 2005/090945 A1 | 9/2005 |
| WO | WO 2007/136818 A2 | 11/2007 |
| WO | WO 2008/010870 A2 | 1/2008 |

OTHER PUBLICATIONS

D.T. Suess and K. A. Prather, "Mass spectrometry of aerosols", Chem. Rev. 99, 3007-3035 (1999).

Y.L. Pan, S. Holler, R. K. Chang, S. C. Hill, R. G. Pinnick, S. Niles, and J. R. Bottiger, "Single-shot fluorescence spectra of individual micrometer-sized bioaerosols illuminated by a 351- or a 266-nm ultraviolet laser," Opt. Lett. vol. 24, No. 1, pp. 116-118 (Jan. 1999).

K. Davitt, Y.-K. Song, W. Patterson, III, A. Nurmikko, M. Gherasimova, J. Han, Y.-L. Pan, and R. Chang, "290 and 340 nm UV LED arrays for fluorescence detection from single airborne particles," Opt. Express vol. 13, No. 23, pp. 9548-9555 (Nov. 2005).

D. R. Burnham and D. McGloin, "Holographic optical trapping of aerosol droplets," Opt. Express vol. 14, No. 9, pp. 4175-4181 (2006).

K. G. Bartlett and C. Y. She, "Single-particle correlated time-of-flight velocimeter for remote wind-speed measurement," Opt. Lett. vol. 1, No. 5, pp. 175-177 (Nov. 1977).

William D. Herzog, Shane M. Tysk, David W. Tardiff, Gregory G. Cappiello, Jasaon M. Jong, Thomas H. Jeys, Ronald H. Hoffeld, Antonio Sanchez and Vincenzo Daneu, "Measurement of aerosol-particle trajectories using a structured laser beam," Appl. Opt. vol. 46, No. 16, pp. 3150-3155 (Jun. 2007).

International Preliminary Report on Patentability issued Aug. 17, 2010, for International Application No. PCT/US2008/001793.

International Search Report and Written Opinion from PCT/US2007/012034, mailed Feb. 7, 2008.

International Search Report and Written Opinion from PCT/US2007/012047, mailed May 7, 2008.

International Search Report and Written Opinion from PCT/US2008/001793, mailed Nov. 21, 2008.

International Search Report from PCT/US2008/001793 mailed Nov. 21, 2008.

* cited by examiner

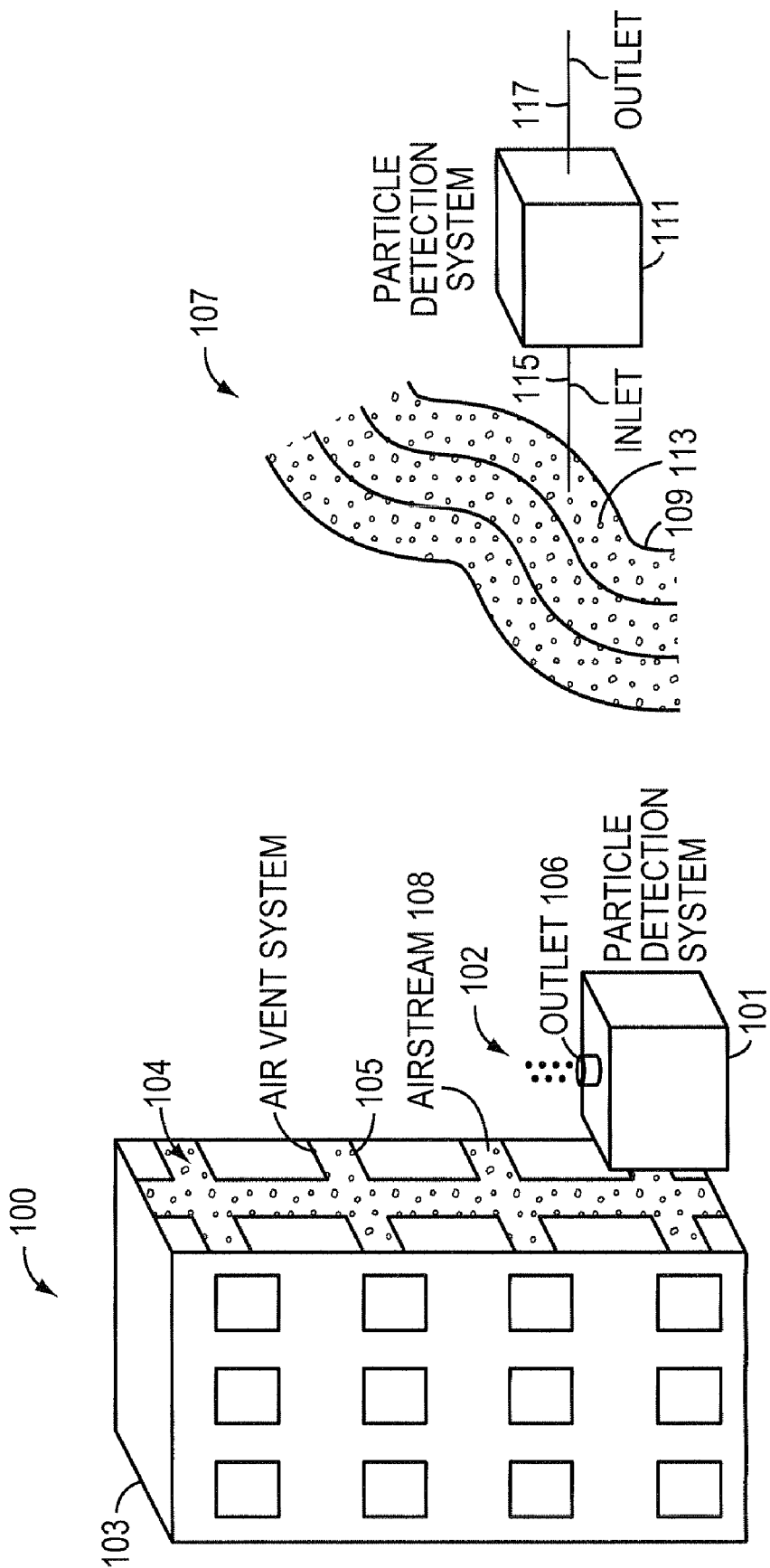

(NOT DRAWN TO SCALE)

METHOD AND APPARATUS FOR DETECTING AND DISCRIMINATING PARTICLES IN A FLUID

GOVERNMENT SUPPORT

The invention was supported, in whole or in part, by a grant FA8721-05-C-0002 from the United States Air Force. The Government has certain rights in the invention.

RELATED APPLICATION

This application is related to U.S. application Ser. No. 11/804,593, filed May 18, 2007, which claims the benefit of U.S. Provisional Application No. 60/802,088, filed on May 18, 2006. The entire teachings of the above applications are incorporated herein by reference.

BACKGROUND OF THE INVENTION

An ability to detect and classify small particles in a fluid stream (air or liquid) is of great use in many fields. For example, detecting harmful particles in air (e.g., outdoors or inside a building) or in water (e.g., a city water supply) may be used to protect people from non-lethal particles, such as mold spores, or lethal particles, such as biological agent particles. In addition, a large class of particle detector systems referred to as flow cytometers are based on the detection and classification of particles in a fluid stream. Typically, such systems detect a particle by illuminating it with radiation (ultraviolet to infrared) and detecting the resulting particle emitted radiation (elastic scattering and/or fluorescence).

SUMMARY OF THE INVENTION

In many flow cytometer systems, the particle emitted radiation is weak and very sensitive photodetectors must be used to detect the radiation. The photomultiplier tube (PMT) is a type of photodetector that is often used to detect weak (low photon rate) radiation. While photomultiplier tube (PMT) devices are often the ideal photodetector for low light applications there are a few drawbacks associated with their use. First PMTs are relatively expensive as compared with other types of photodetectors such as the semiconductor photodiode or charged coupled device (CCD) detector. Second, PMTs typically require high voltage (about 1000 Volts) for proper operation. Such voltages can be dangerous to people and require protective measures. Third, PMTs are not as physically robust as other types of photodetectors. For example, shock or exposure to moderate light levels can permanently damage a PMT.

Existing flow cytometer systems tightly confine the particle flow stream in order to ensure optimal particle illumination and detection of particle radiation. In addition these systems detect only one particle at a time. This tight flow confinement and one particle at a time detection methodology substantially limit the fluid flow rate and the number of particles that can be interrogated per unit time.

A system and method for particle detection, according to example embodiments of the present invention, is presented. This system utilizes detector arrays for detecting the light emission from particles in a flow stream and may also utilize light source arrays for selective illumination of the particles. Each element of the detector array is sensitive to particle emission from a particular sub-element of the air flow sample volume. Similarly each element of the light source array illuminates a particular sub-element of the air flow sample volume. This system has several advantages over traditional particle detection or flow cytometry systems. These advantages include the use of a lower cost and more robust photodetector as compared with the photomultiplier tube, increased versatility in the detection of the particle emission, increased air flow handling capability, simultaneous multiple particle detection, and when using light source arrays, increased particle emission signal-to-noise ratio, and reduced system power consumption.

The system for particle imaging and detection may comprise a light source to provide light to illuminate at least a portion of a sample volume, through which particles flow to produce particle radiation caused by a particle being illuminated by the light. The system may also provide a detector array and optical system positioned to image the particle radiation at a substantially fixed location on the detector array. The system may also include a detector array read-out mechanism for measuring the particle radiation that is incident on the detector array. The detector array may include a Charge Coupled Device (CCD) or a Geiger-mode avalanche photodiode (GM-APD) array. The particle radiation may include elastically scattered light and luminescent light.

The system may also comprise a processor coupled to the detector array to discriminate one type of particle from other types of particles in the sample volume based on measured particle elastic scattering and luminescence signals. The detector array and processor may be configured to detect either a portion of the elastically scattered light or a portion of luminescent light at different wavelengths, or a combination of both.

The system may further comprise a database configured to be used by the processor to store signals representative of different particles in the particle flow. The processor may be configured to generate a signal to notify a user of the presence of a type of particle, whose representative signals may have previously been stored in the database or whose representative signals may not have been stored in the database and that normally does not flow through the sample volume.

The light source may be a multiple wavelength light source configured to have wavelengths selectively activated. Additionally, a detector array controller may be employed to shift charge, produced by the particle radiation, on the detector array to read out the charge and to allow the charge from multiple sequential illumination wavelengths to be separated.

The light source may also comprise an array of light emitters. The system may also comprise a position sensitive detector (PSD) beam subsystem to locate a position of the particle in the sample volume. The PSD beam system is described in U.S. patent application Ser. Nos. 11/804,593 and 60/927,832, which are all incorporated by reference. The known position of the particle may be used to activate the light array sub-element that will illuminate the particle and the detector array read-out procedure.

A processor may be used to estimate the substantially fixed location of the particle radiation on the detector array based on the position of the particle in the sample volume. Additionally, an array controller may be employed to add, or bin, charge produced on the detector array by the particle radiation based on knowledge of the substantially fixed location in which this charge resides.

The system may also comprise an array controller configured to add, or bin, charge produced on the detector array by the particle radiation. In at least one embodiment, a processor is coupled to the detector array and configured to identify the substantially fixed location through at least one imaging of the particle radiation, and the processor may further be configured to selectively bin charge only in the substantially fixed location identified by the processor.

The system may also include an optical assembly to direct the particle radiation toward the pixel based detector array substantially free from illuminating the detector array with light from the light source.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 1 and 2 are diagrams with examples of particle detection systems;

DETAILED DESCRIPTION OF THE INVENTION

Figure 3A:
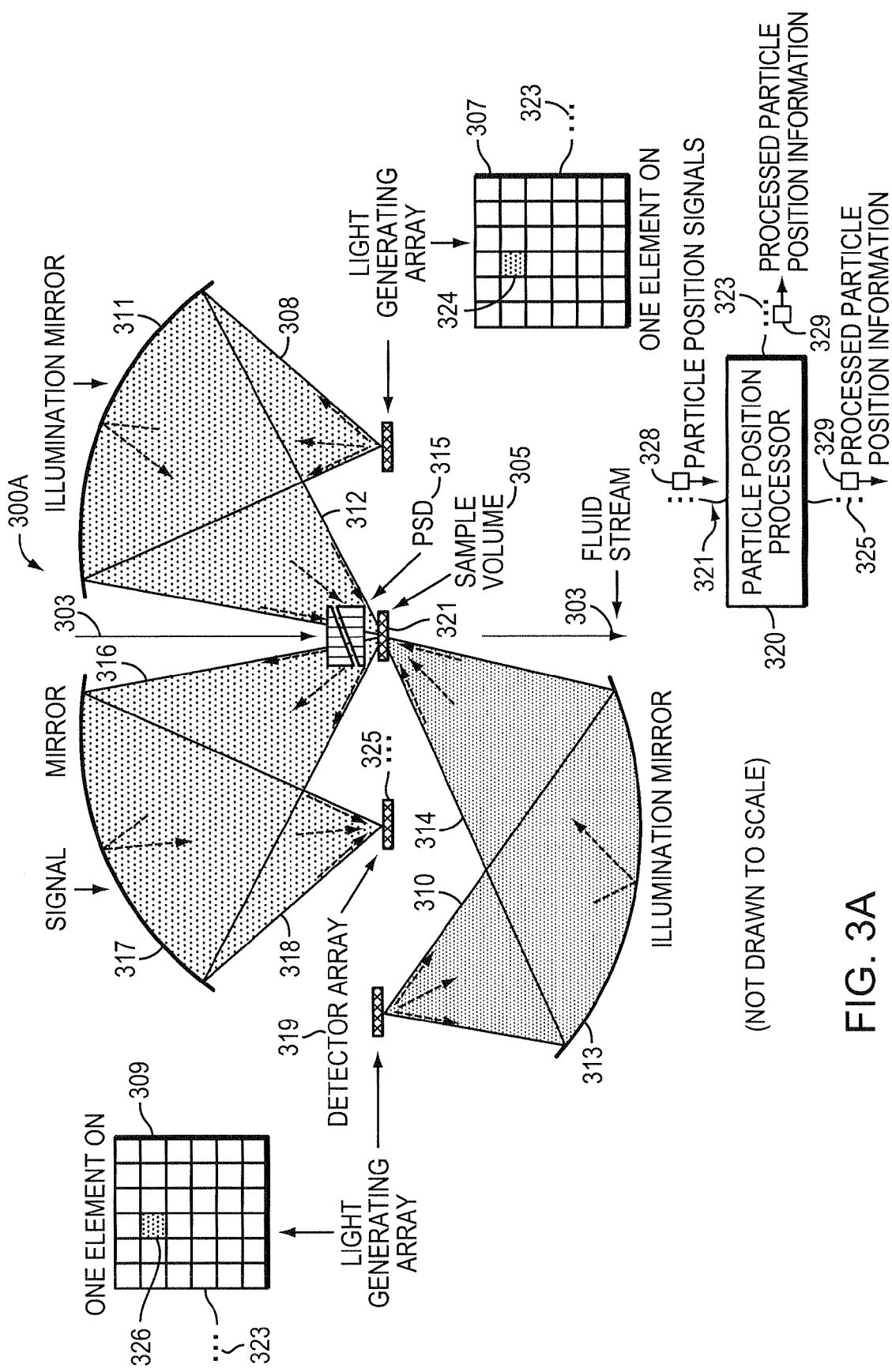
FIG. 3A is an optical schematic diagram of a particle detection system featuring optical mirrors according to an embodiment of the present invention.

A description of example embodiments of the invention follows.

FIG. 1 provides an example 100 of a particle detection system 101. The particle detection system 101 may be situated to detect particles 104 in an air vent system 105 of a building 103. The particle detection system 101 includes an inlet (not shown) in which an airflow enters the particle detection system 101. An outlet 106 may be used as a pathway to shunt the airflow from the detection system 101. The detection system 101 may be used to control air duct valves within the building in order close off the building from outside air or from other parts of the building if particles 102 detected are deemed unsafe for breathing.

As another example, a liquid stream may also need to be evaluated. For instance, a water reservoir may need to be continuously monitored to ensure harmful particles are not introduced into a water supply.

FIG. 2 provides an example 107 of a particle detection system 111 detecting particles 113 in a liquid stream 109. The particle detection system 111 may include an outlet 117 and an inlet 115 used to supply a sample of the liquid flow 109 to the particle detection system 111. The detection system may be used to control water pipe valves in order to close off the water supply or shunt in different water supplies if particles are deemed unsafe.

Figure 4A:
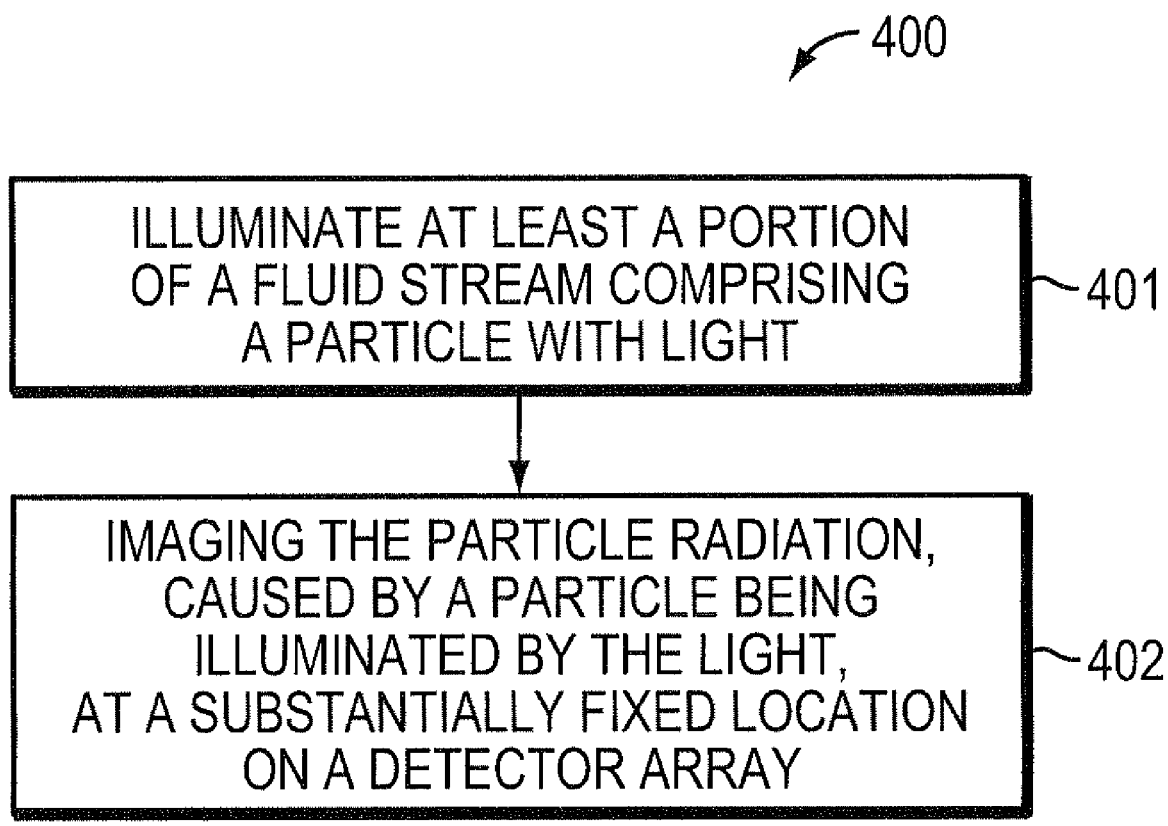
FIG. 4A is a flow chart providing an introductory overview of operations of a particle detection system according to an embodiment of the present invention.

System Overview:

FIG. 3A provides an example of a particle detection system 300A according to an embodiment of the present invention. FIG. 4A shows a diagram 400 of an overview of operations that may be taken by the detection system 300A. Referring to FIG. 3A with some reference to FIG. 4A, the detector system 300A may be placed in the path of a fluid stream 303, which may include particles (not shown). It should be appreciated that air, water, vapor, liquids, or any other known transparent fluid, may compose the fluid stream 303.

Light generating arrays 307 and 309 may be used to illuminate a sample volume 305 of the fluid stream 303, or a volume 305 through which a sample of the fluid stream 303 passes. The pixel light generating arrays 307, 309 may employ light emitting diodes (LEDs), lasers, ultra violet light source, or any other known light source. The light generating arrays 307, 309 may also generate light at multiple wavelengths, and may provide illumination by selectively using a light of a specific wavelength. Additionally, it should be appreciated that although two light generating arrays 307, 309 are shown in the system 300A, any number of light arrays may be employed, including one.

The illumination light generating arrays 307 and 309 may be used to direct diverging light 308 and 310, respectively, towards illumination mirrors 311 and 313, respectively. The illumination mirrors 311 and 313 may be focusing mirrors, for example, elliptical or concave mirrors, allowing converging reflected light 312 and 314, respectively, to be focused on a spot or, in one example case, sample volume 305 (FIG. 4A, 401). The illumination mirrors 311 and 313 may be configured such that no illuminating light (308 and/or 310) or no reflected light (312 and/or 314) is received by the array detector 319. It should be appreciated that any form of mirror or optics may be employed to direct the light 308, 310 toward the sample volume 305. Alternatively, the light generating arrays 307, 309 may directly project light beams at the sample volume 305.

As a result of illuminating the particles in the flow 303 within the sample volume 305, a diverging particle emitted light 316 may be produced. The particle emitted light 316 may be a result of elastic scattering and/or luminescence from the particle.

A PSD light beam 315 may be used to find the particle position (in the sample volume 305). In FIG. 3A, the PSD light beam propagates transverse to the plane of the drawing. Particle position signals 328 are received by the particle position processor 320 which generates the particle position information 329. With knowledge of the particle position, the appropriate sub-element of the light source array 307 and/or 309 may be used to illuminate the particle in an efficient manner, which may also serve to improve the signal-to-noise ratio of detecting particle radiation, caused by a particle and substantially only a small volume containing the particle being illuminated by the light.

The particle position processor 320 may be connected to the PSD 315 via a connection 321. The particle position processor 320 may also be connected to the pixel light arrays 307 and/or 309 via a connection 323. It should be appreciated that the connections 321 and 323 may be in the form of any data connection known in the art, for example, wireless or optical data connections. It should also be appreciated that, in an alternative embodiment, the particle position processor 320 may also be an internal component of the PSD 315. The PSD 315 may supply the particle position processor 320 with particle position signals 328. The particle position processor 320 may, in turn, process the particle position signals 328 in order to determine a precise location of the particle and therein transfer the processed particle position information 329 to the pixel light array 307, 309, or the controller 401 (in FIG. 4B) in real time.

Using the processed particle position information 329 supplied by the particle position processor 320, in one example embodiment of the invention, a selection of light generating sub-elements, for example LEDs, within the light generating array 307 may be made, allowing only the sub-element which is required to illuminate the particle to be used. As is shown in FIG. 3A and FIG. 3E as examples, only a single sub-element 324 and 326 from each light generating array 307 and 309 respectively is activated. Therefore, only the portion of the light generating array which directly illuminates the particle in the sample volume 305 is utilized in this example embodiment. Thus, employing the PSD 315 and particle position processor 320 in the operation of the pixel light array 307, 309 may dramatically reduce the power consumption of the particle detection system 300A.

Alternatively, the light generating array 307, 309 may employ a single light source which may be mechanically moved based on the processed particle position information 329 provided by the particle position processor 320 via the PSD 315, or a mirror or other optical element between the single light source and the particle may be operated to selectively illuminate the particle.

As the particles in the sample volume 305 pass through the reflected illumination light 312, 314, a diverging light scattering 316 is produced as a result of a elastic scattering and luminescence of the particles. Using a signal mirror 317, the diverging particle light 316 may be reflected, forming a converging reflected light 318, and directed to a detector array 319.

It should be appreciated that the signal mirror 317 may be a dispersive mirror, allowing the reflected particle light 318 to separate into spectral components with different wavelengths. Thus, different spectral readings, with the readings being in different spatial locations, may be obtained. It should also be appreciated that any other optical elements may be employed in place of the signal mirror 317 which focus the particle signal onto the detector array; for example, an optical lens may be used.

The detector array 319 may be configured to receive the particle light 318 reflected from the signal mirror 317. The detector array may be used to image and measure an intensity of particle radiation produced by the particle light 318. The detector array 319 may be, for example, a Charge Coupled Device (CCD) or a Geiger-mode avalanche photodiode (GM-APD) array. It should be appreciated that any other form of light detection array may also be employed.

The particle position processor 320 may also be connected to the detector array 319 via a connection 325. It should be appreciated that the connection 325 may be in the form of any data connection known in the art, for example, a wireless or optical data connection. The particle position processor 320 may be configured to supply processed particle information 329 to the detector array 319. Using the processed particle position information 329, the detector array 319 may employ "smart" adding or binning of the particle signals, where only the portions of the detector array 319 that are expected to receive particle radiation are added or binned. This method of reading out the particle signals contrasts prior art methods in which either the entire detector array is read out element by element or predetermined areas are added or binned but these areas do not randomly change from one read out to the next on a fast time scale.

The detection system 300A may be configured to provide a longitudinal imaging of the particles along their path of motion. The optical axis of the imaging system in the sample volume may be substantially in the same direction as the particle motion. Therefore, the particle signal which is imaged on the detection array 319 is in a substantially small area. In contrast, transverse imaging of the moving particle distributes the particle signal charges over many more detector sub-elements as the particle motion traces a path across the detector array. If each of the detector sub-elements have a separate associated noise then the signal to noise ratio is worse for transverse imaging than for longitudinal imaging.

However, the disadvantages of transverse imaging may be overcome with the use of time delay and integration (TDI). TDI is a well know technique for acquiring low noise signals from an object moving relative to a detector array. In the application of TDI, the relative movement of an object is synchronized with the reading or binning of signal on the detector array so as to de-blur the image of the object. For example, in airborne imagery a CCD detector may be configured to move the signal charge on a CCD in the same direction and speed as the ground image travels across the CCD. This compensatory motion essentially freezes the motion of the ground and provides an un-blurred image.

In example embodiments, the detector array 319 may employ charge shifting with the use of TDI in order to compensate for motion of the particle image across the detector array. Thus, as the particles travel across the length of the detector array, a TDI charge shifting technique may be used to shift the charge at the same rate that the particle is traveling. The speed at which the particle is traveling and the location of the particle may be determined with the use of the PSD system. Using TDI in conjunction with the PSD allows the particle signal to collect in a small subset of the detector array and allows appropriate binning of the particle signal so as to maximize the signal to noise ratio of the particle signal.

FIGS. 3B-3E provide alternative embodiments of the detection system 300a of FIG. 3A featuring optical lenses instead of optical mirrors.

Figure 3B:
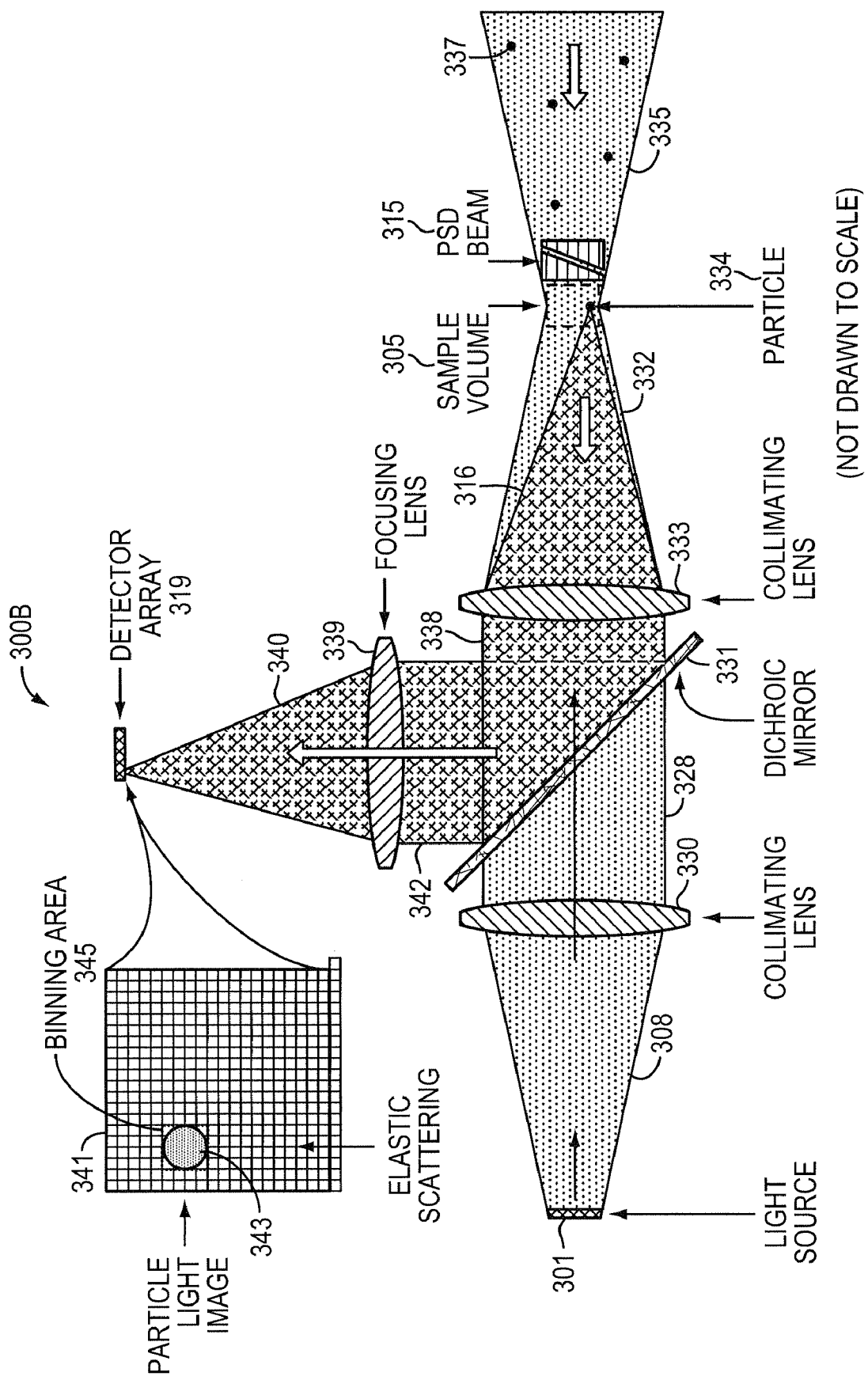
FIGS. 3B-3E are optical schematic diagrams of various particle detection systems featuring optical lenses according to another embodiment of the present invention.

FIG. 3B illustrates a particle detection system 300B configured to detect particles 337 traveling in a fluid stream 335. The detection system 300B may feature a single element light source 301 configured to emit a diverging illumination beam 308. A collimating lens 330 may be configured to receive the diverging illumination beam 308 resulting in a substantially collimated beam 328. The substantially collimated beam 328 may then pass through a dichroic mirror 331. A dichroic mirror is a filter configured to transmit selectively and reflect light of a specific wavelength or a specific band of wavelengths.

Upon passing through the dichroic mirror 331, the substantially collimated beam 328 may then be focused by a lens 333 into the sample volume 305. The PSD system 315 may be used to turn on the single element light source 301 once a particle 334 is in the sample volume. A diverging particle light 316 is produced as the particle is illuminated by the light beam 332. The diverging particle light 316 may then be substantially collimated 338 via a collimating lens 333 and thereafter directed towards the dichroic mirror 331. The dichroic mirror 331 may be configured to reflect the substantially collimated particle light 338 toward a focusing lens 339 and thereafter focused onto the detector array 319. A zoomed-in view 341 of the detector array 319 shows an image of the particle light 343 formed on a portion of the detector array. A binning area 345 may be predefined with the use of the PSD 315 to "smart" bin only the area including the image of the scattered light 343.

Figure 3C:
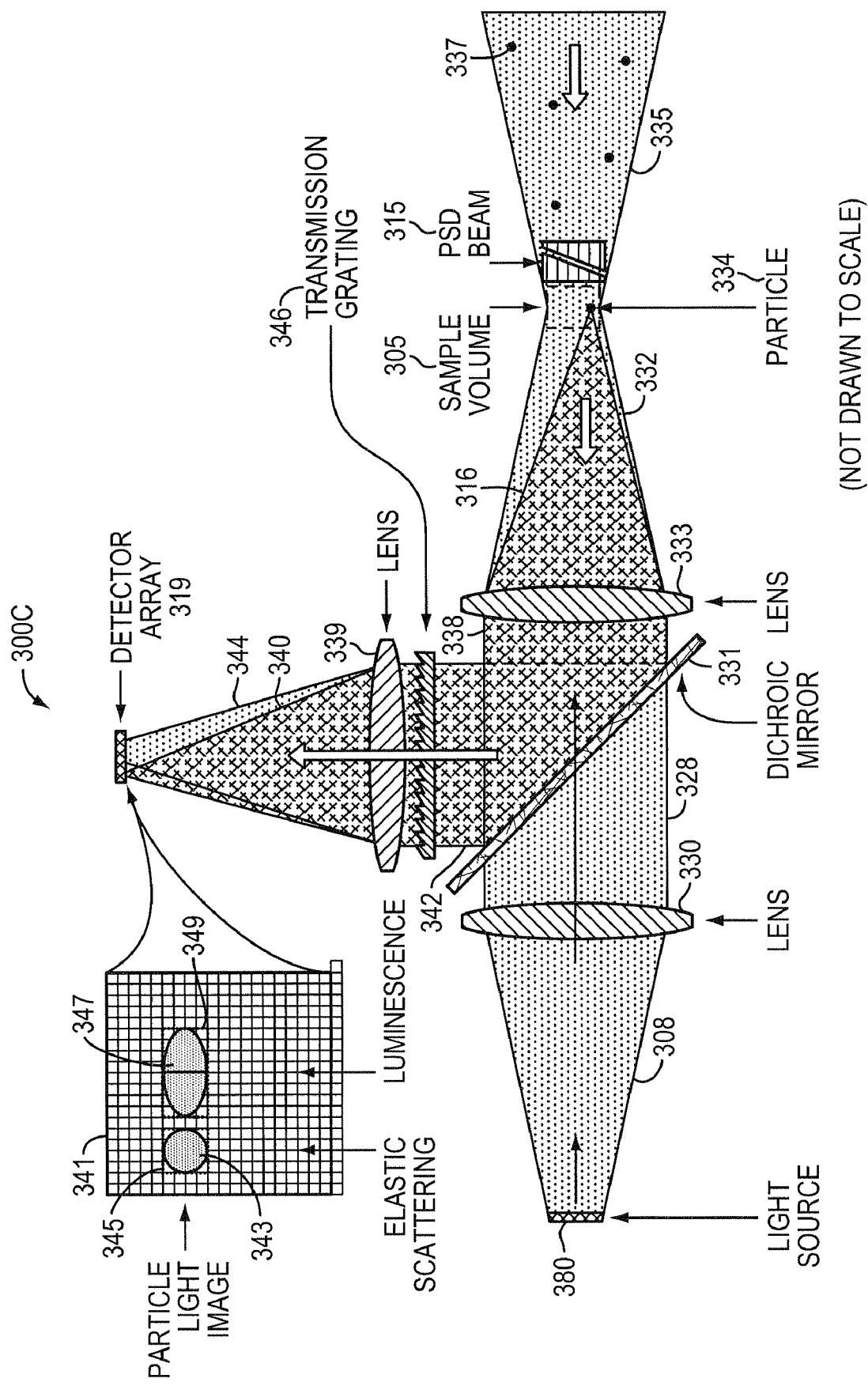

FIG. 3C illustrates a particle position detection system 300C similar to the detection system 300B of FIG. 3B with the addition of a transmission grating 346. The transmission grating 346 may be used to obtain luminescent scattering information of the particle position. The transmission grating 346 may be configured to disperse the reflected and collimated particle light 342. By wavelength dispersing the particle radiation onto the light pixel detector 319 it is possible to measure the particle luminescence emission spectrum. This spectrum provides additional information that may be used to discriminate one type of particle from another. Upon passing through the transmission grating 346, the particle light 342 may be dispersed into an elastic scattering component 340 and a luminescence component 344 (at a range of wavelengths greater than the elastically scattered light 340), where the components may be dispersed at different angles in order to prevent overlapping images on the light pixel array detector 319. It should be appreciated that the particle light 342 may also be dispersed with the use of any other dispersion mechanism known in the art, such as a prism or reflection grating. The zoomed in view of the light pixel array detector 341 features a luminescence image 347 in addition to the elastic scattering image 343. With use of the PSD 315, a binning area 349 may also be defined for the luminescence image 347 in the "smart" binning method. In this case the elastic scattering is binned into one region 345 and the luminescence image 347 is binned into two regions 349.

Figure 3D:
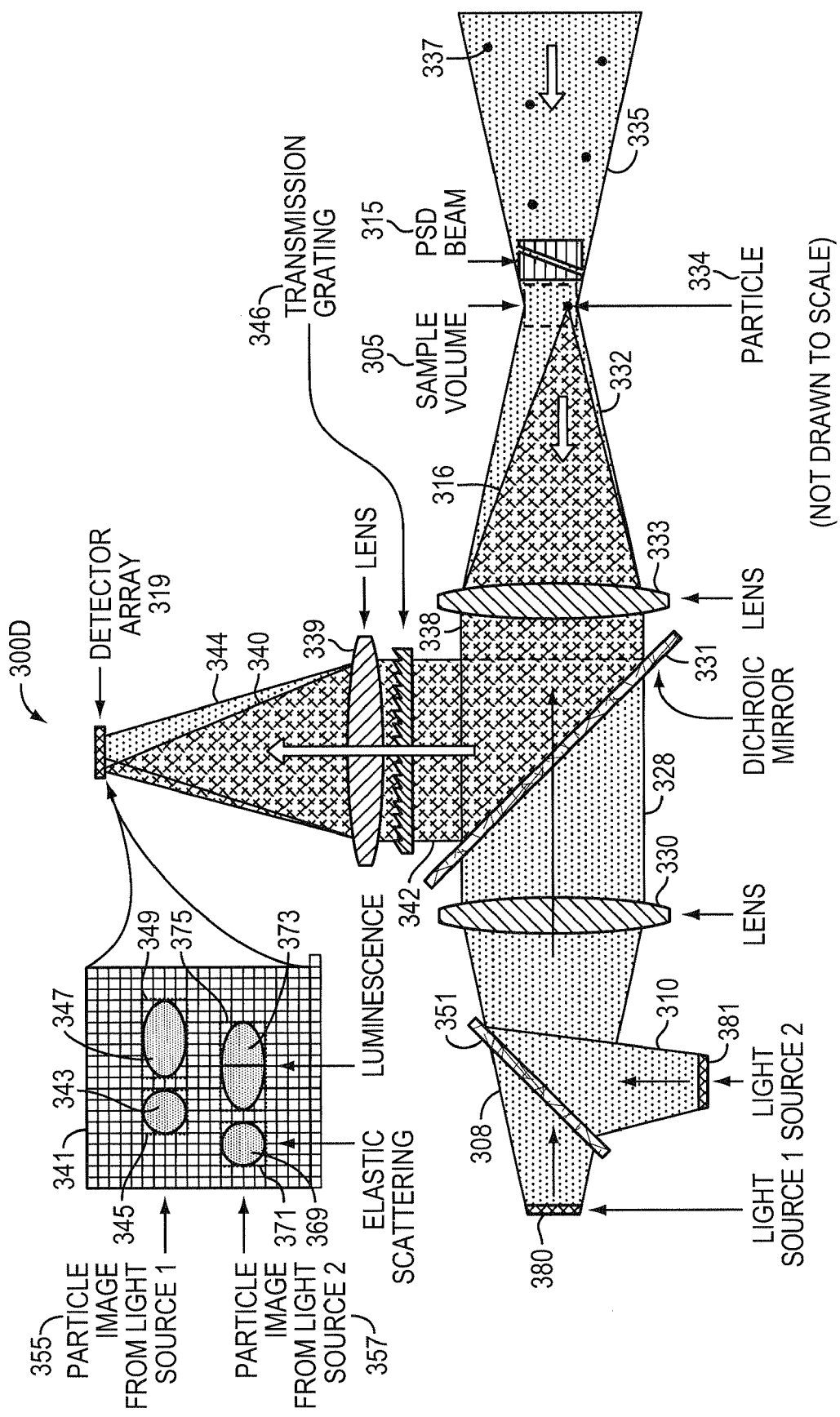
Figure 3E:
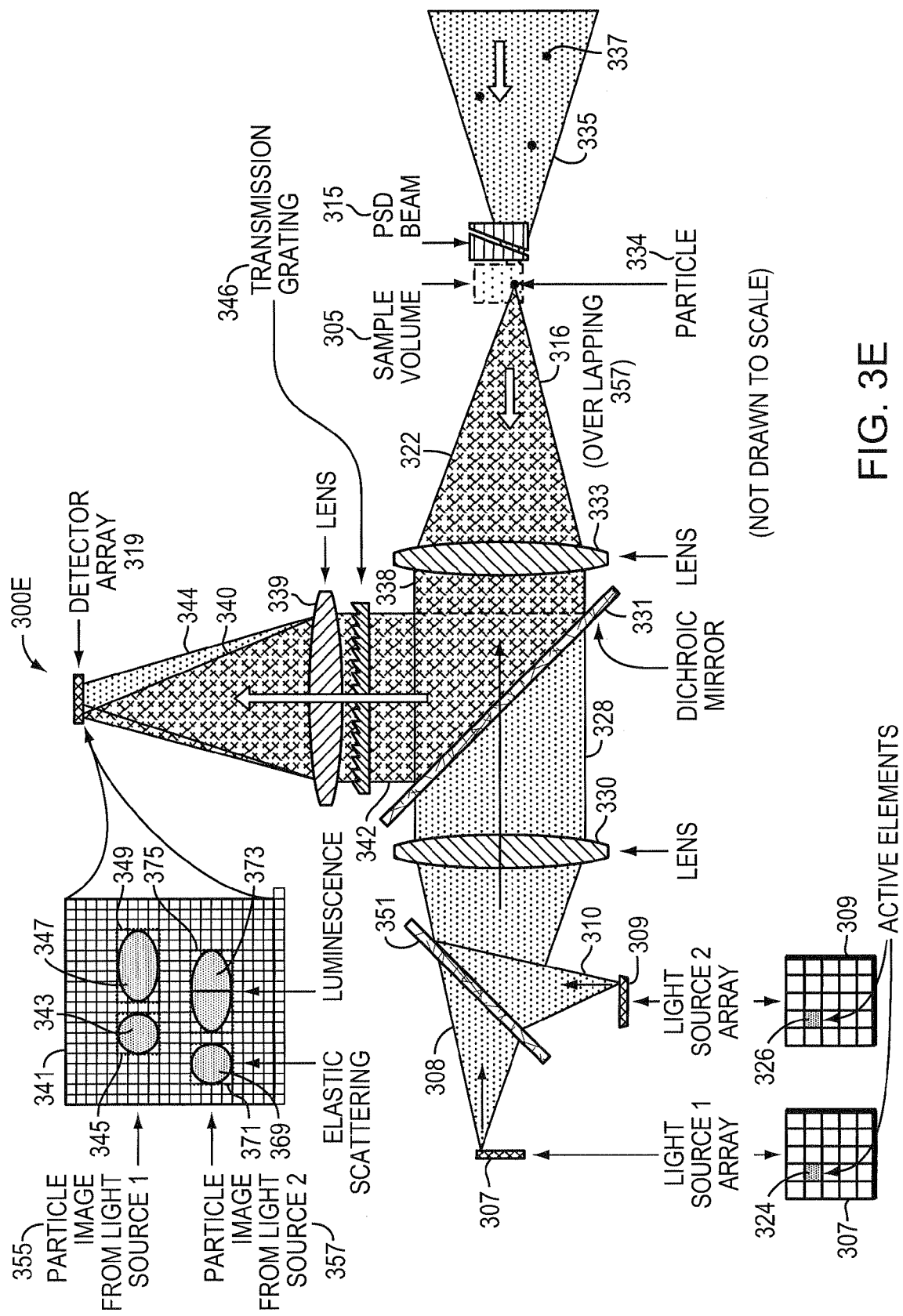

FIG. 3D illustrates a particle position detection system 300D similar to the detection system 300c of FIG. 3C with the addition of an optical reflecting device 351 and a second light source 381. The alternative configuration of the particle detection system 300D shown in FIG. 3D may be ideal for sequential illumination of the particle with different wavelengths of light. Particle discrimination may be further enhanced by sequentially illuminating the particle with different wavelengths while the particle 334 is in the sample volume 305, and separately recording the elastic scattering and luminescence images obtained from the beams of different wavelengths on different locations of the detector array 319.

The first and second light source, 380 and 381, respectively, are, in this example embodiment, sequentially illuminated, as opposed to simultaneously illuminated, in order to avoid confusion as to which particle signal is due to which illumination beam. An optical reflection device 351 may be configured to direct the sequentially illuminated light beams 308 and 310 by transmitting the light from the first light source 380 and reflecting the light from the second light source 381, respectively. After the elastic and luminescent images 355 from the first light source 380 have been recorded, the recorded image, or recorded charge, may be shifted along the detector surface in anticipation of an image 357 due to light scattering provided by the second light source 381. Knowledge of where to shift images on the detector surface may be obtain with use of the PSD 315. In this implementation, light source 1 380 may be turned on when a particle is in the sample volume. Particle emission induced by light source 1 380 may result in an elastic scattering signal 369 and a luminescence signal 373. While the particle is still in the sample volume, light source 1 380 may be turned off and light source 2 381 turned on. Between these sequential illuminations of the particle, the particle signal charges 369 and 373 on the detector array may be shifted far enough to avoid overlap with the particle signal resulting from turning on light source 2. After illumination by both light sources 380 and 381 the particle signals are binned into regions associated with light source 1 induced elastic scattering 371, light source 1 induced luminescence 373, light source 2 induced elastic scattering 345, and light source 2 induced luminescence 349.

FIG. 3E illustrates a particle position detection system 300E similar to the detection system 300D of FIG. 3D with the addition of the first and second light source arrays 307 and 309, as shown in FIG. 3A. This implementation is the same as implementation 300D except that the light sources 307 and 309 are array light sources. Based on particle position information from the particle position processor only the sub-element of light source 1 and then light source 2 are activated to illuminate only the sub-volume in which the particle resides. This has the advantage of reducing the amount of light that passes through the sample volume while at the same time not reducing the amount of light incident on the particle. In this way the background noise light incident on the detector is reduced and therefore the measurement signal to noise ratio is increased. In addition, because only a single sub-element of light source array 1 and 2 are turned on, much less power is consumed.

It should be appreciated that the particle position processor 320 shown in FIG. 3A may be implemented in any of the alternative detection configurations illustrated in FIGS. 3B-3E.

Figure 4B:
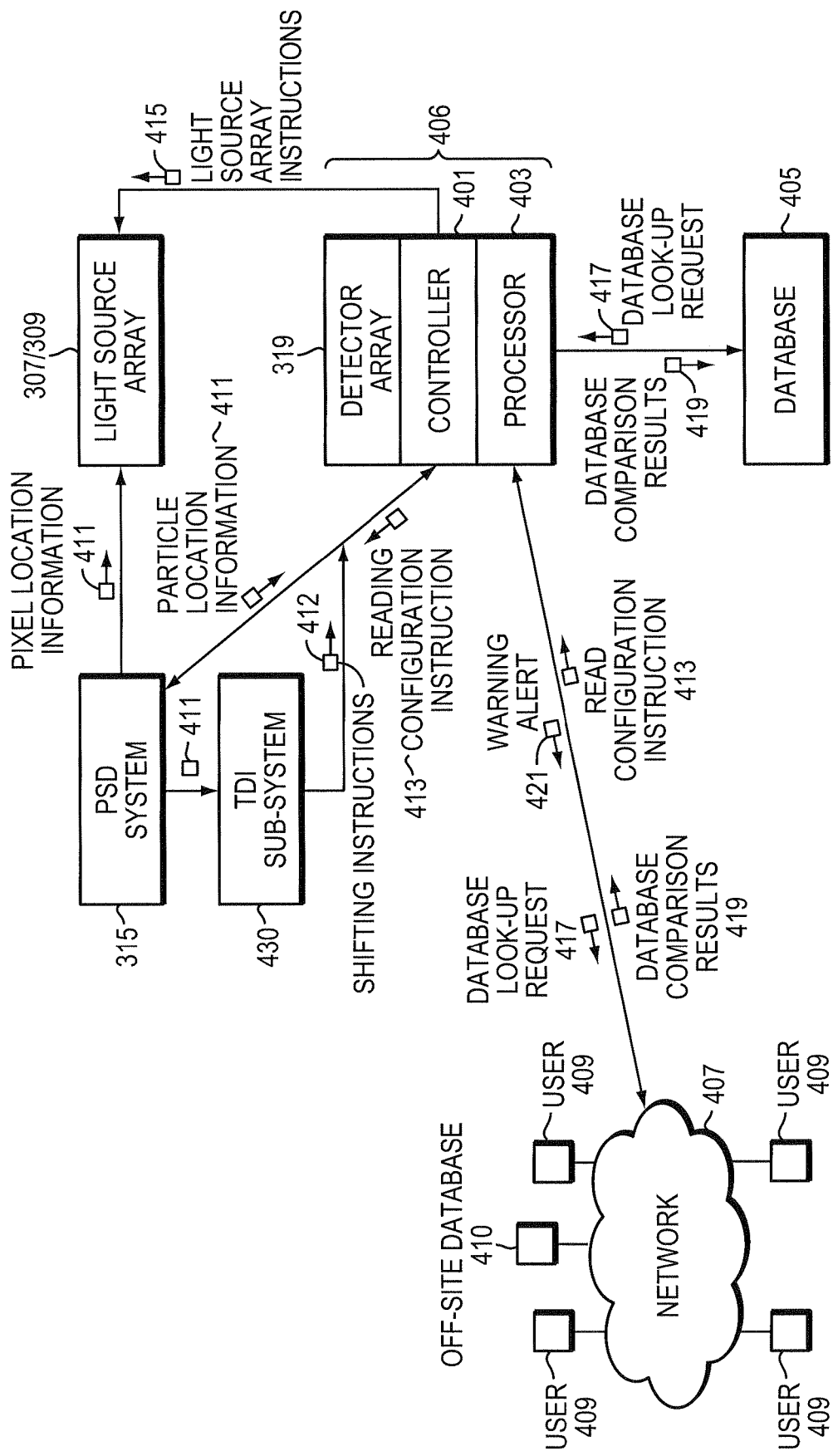
FIG. 4B is an apparatus block diagram providing an overview of a relationship between various system components according to an embodiment of the present invention.

FIG. 4B is a block diagram that provides an example overview of possible relationships between the various system components in an embodiment of the present invention. The PSD system 315 may be used to send particle location information 411 to light source array(s) 307 and/or 309. This information may be used to select which sub-element of the light source to activate. Additionally, the particle position information may provide instructions for selected wavelength (s) or on/off settings.

The PSD system 315 may also provide information to a detector array system 406, which may comprise the detector array 319, a controller 401, and a processor 403. The PSD system 315 may send the detector array system 406 particle location information 411. The particle location information 411 may be used in a "smart" binning process, in which only selected areas of the detector array 319 are summed, or binned, and then read out. The pixel detector array system 406 may also send read configuration instructions 413 to the PSD system 315. For example, consider a case in which the detector array system 406 is configured to measure a particular particle in the sample volume in a continuous manner. The detector array system 406 may send the request 413 to the PSD system to track and monitor continuously that particular particle. Continuously tracking the particle allows the detector array 319 to add, or bin, the areas of the detector array 319 where the particle signal appears. This "image stabilization" mode of operation has the advantage that the particle need not travel along the optical axis of the imaging system because the particle signal is made to track the image of the particle on the detector array.

In the case of transverse imaging, the PSD system 315 may also be in communication with a time delay and integration (TDI) sub-system 430. The PSD system 315 may also send particle location information 411 to the TDI sub-system. The TDI sub-system 430 may be with the controller 401. The TDI sub-system may send shifting instructions 412 to the controller 401, which may be used to aid the controller in shifting the charge on the detector array. With knowledge of the particle position, the TDI sub-system may determine the rate at which the charge should be shifted when the particle radiation is imaged transversely, and the location and size of the binning region may be chosen to maximize the particle signal to noise ratio.

The detector array system 406 may also send pixel illumination instructions 415 to the light source array(s) 307 and/or 309. The illumination instructions 415 may include instructions on illuminating the particles with a specific wavelength and, optionally or alternatively, on/off commands. Similarly the detector array system 406 may provide instructions to the light source array (s) 307 and/or 309 to track the particle in the sample volume.

The detector array system 406 may also be in communication with a database 405. The detector array system 406 may send a database look-up request 417 to the database 405. This look-up request 417 may be used to compare the currently measured signals with previously measured or simulated signals or stored in the database. This comparison may be used in the classification and identification of particles. The database 405 may send the comparison results to the detector array system 406 so as to influence the binning pattern of particle signal acquisition. It should be appreciated that the database 405 may be an adaptive database and store any information deemed useful for the discrimination of particles.

The detector array system 406 may also send a database look-up request 417 to an offsite database 410 via a network 407. The offsite database may also send comparison results 419 to the detector array system 406. A user 409 may send read configuration instructions 413 to the detector array system 406, for example, if it is useful to detect a particular particle. The detector array processor 403 may send a warning alert 421 back to the user 409 that a detection of the particle has occurred. It should be appreciated that the data links between the various system components of FIG. 4B may be any form of data linkage well known in the art (e.g., fiber optical connections, wireless, etc.).

Figure 5A:
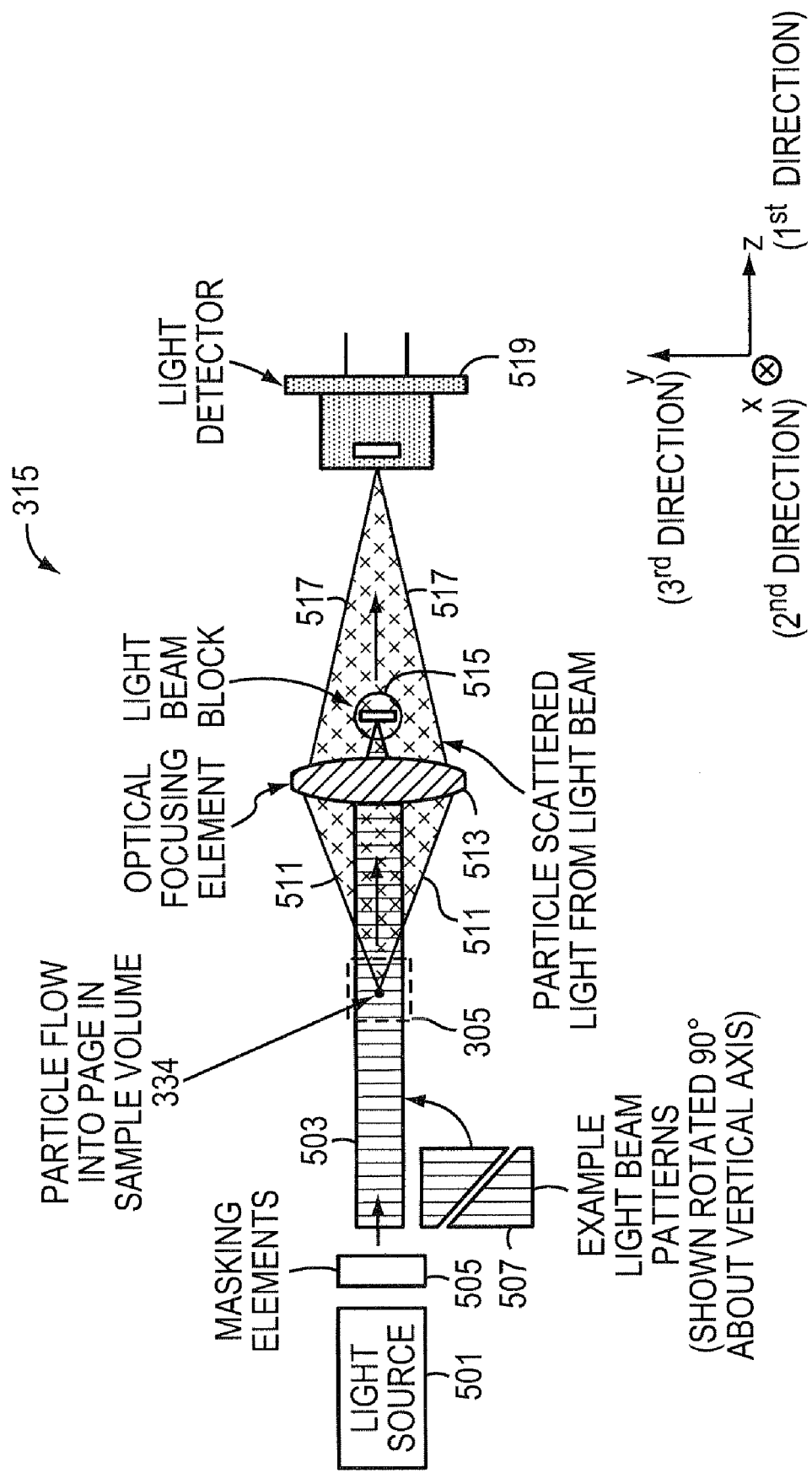
FIGS. 5A and 5B are diagrams of a position sensitive detector (PSD) system according to an embodiment of the invention.

Position Sensitive Detector (PSD):

FIG. 5A provides an example of a position sensitive detector (PSD) 315 according to an embodiment of the present invention. The PSD 315 may include a light source 501 configured to emit a propagating beam 503, also referred to herein as an "illuminating light beam," traveling in the z dimension, or a first dimension. A masking element 505 may be coupled to the light source 501 to produce a light beam pattern 507 also referred to herein as an "illuminating pattern," in x and y dimensions, or second and third dimensions, respectively. It should be appreciated that the light beam 507 shown in FIG. 5A is rotated 90 degrees about its vertical axis as represented in FIG. 5A. It should also be appreciated that instead of the light beam pattern shown (507), any other light beam pattern may be employed in the PSD system 315.

The propagating light beam 503 defines the beam pattern 507 at a sample volume 305 within a particle flow 335. The sample volume 305 may be configured to "receive" the flow in the x axis, or the second dimension. As the particles 334 in the sample volume 305 pass through the propagating beam 503, defining the beam pattern 507, a diverging light scattering 511 is produced as a result of a collision of photons with the particles passing through the beam pattern 507.

The diverging light scattering 511 has a temporal profile that is a function of the beam pattern 507. For example, for the beam pattern 507, the temporal profile exhibits a first period of signal (i.e., scattering), short period of no or very low signal as the particle passes through the gap in the beam pattern, and then a second period of signal. Accordingly, the temporal profile has a timing indicative of the particle's position in the sample volume 305 in the y, or third, dimension. An optical focusing element 513 may be used to focus the produced diverging scattered light 511, resulting in converging scattered light 517. An optical beam blocker 515 may be used to block the propagating beam 503, thereby preventing the propagating beam 503 from directly reaching the light detector 519 and, thus, preventing detector saturation. The converging scattering light 517 may be focused onto the light detector 519 for detection. It should be appreciated that the configuration shown in FIG. 5A of the PSD 315 is merely an example. Any other dimensional configuration may be employed, preferably with the first, second, and third dimensions orthogonal or non-orthogonal to one another.

Figure 5B:
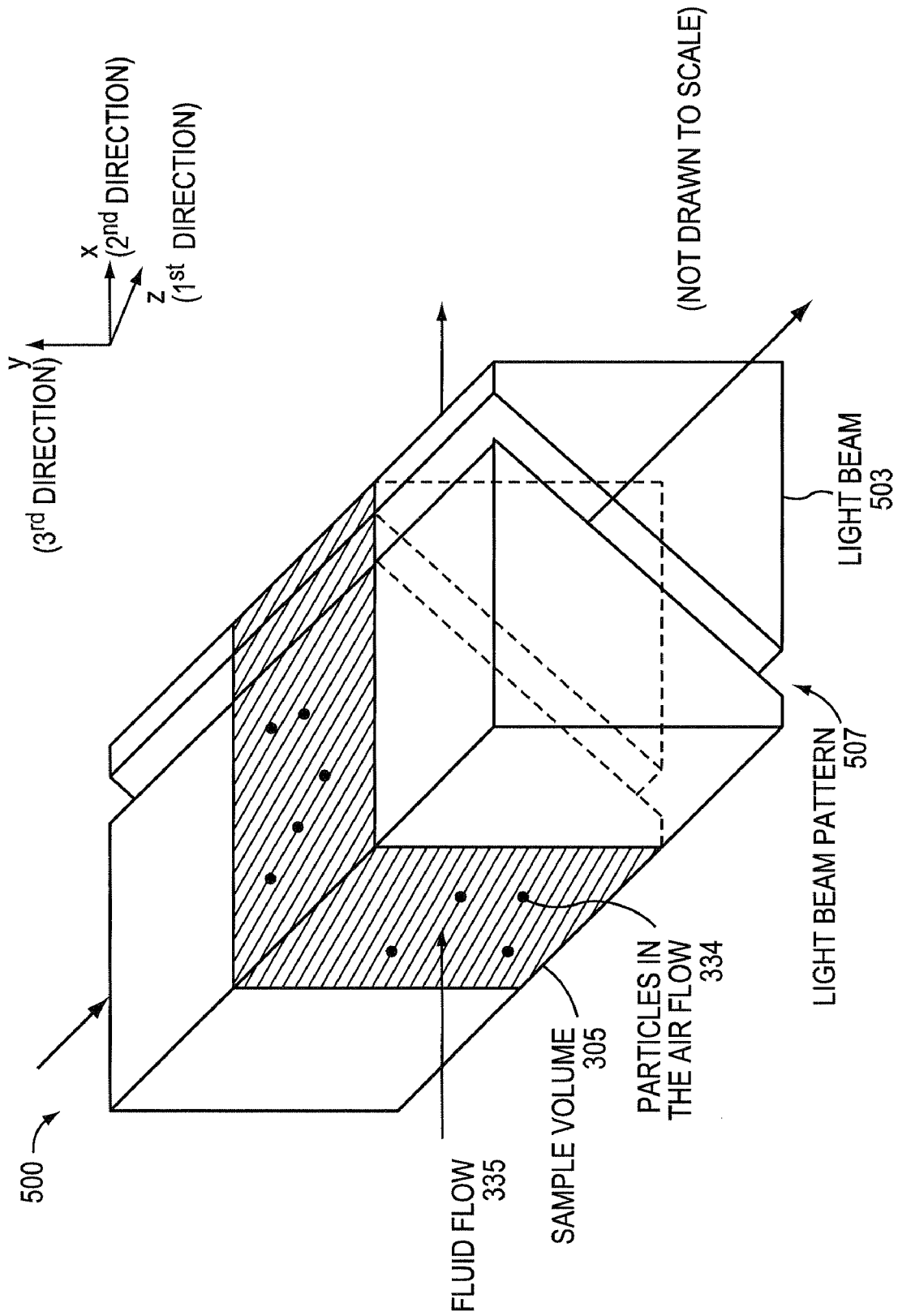

FIG. 5B provides an expanded view 500 of the intersection of the particle fluid flow 335 and the propagating light beam 503, resulting in a sample volume 305. The propagating light beam 503 may be configured to travel in the z, or first, dimension. As is shown in FIG. 5B, the propagating light beam 503 may define a light beam pattern 507 similar to the pattern 507 shown in FIG. 5A. The light beam pattern 507 may, for example, be defined by a square shaped beam with a center diagonal region having an intensity that is substantially equal to zero or substantially less than the intensity of the surrounding portion(s) of the light beam pattern. The fluid flow 335 may be transmitted in the x, or second, dimension. The sample volume 305 may include any number of particles 334 traveling in the particle fluid flow 335. However, it is expected that only one particle at a time will pass through the sample volume 305 or, if more than one particle passes through at a time, they pass through at positions sufficiently distinguishable from each other. It should be appreciated that any geometrical configuration may be employed, provided that the first, second, and third dimensions are orthogonal to each other, in a preferred embodiment. It should also be appreciated that the illumination pattern may be defined by any varying light property, such as polarization.

Figure 5C:
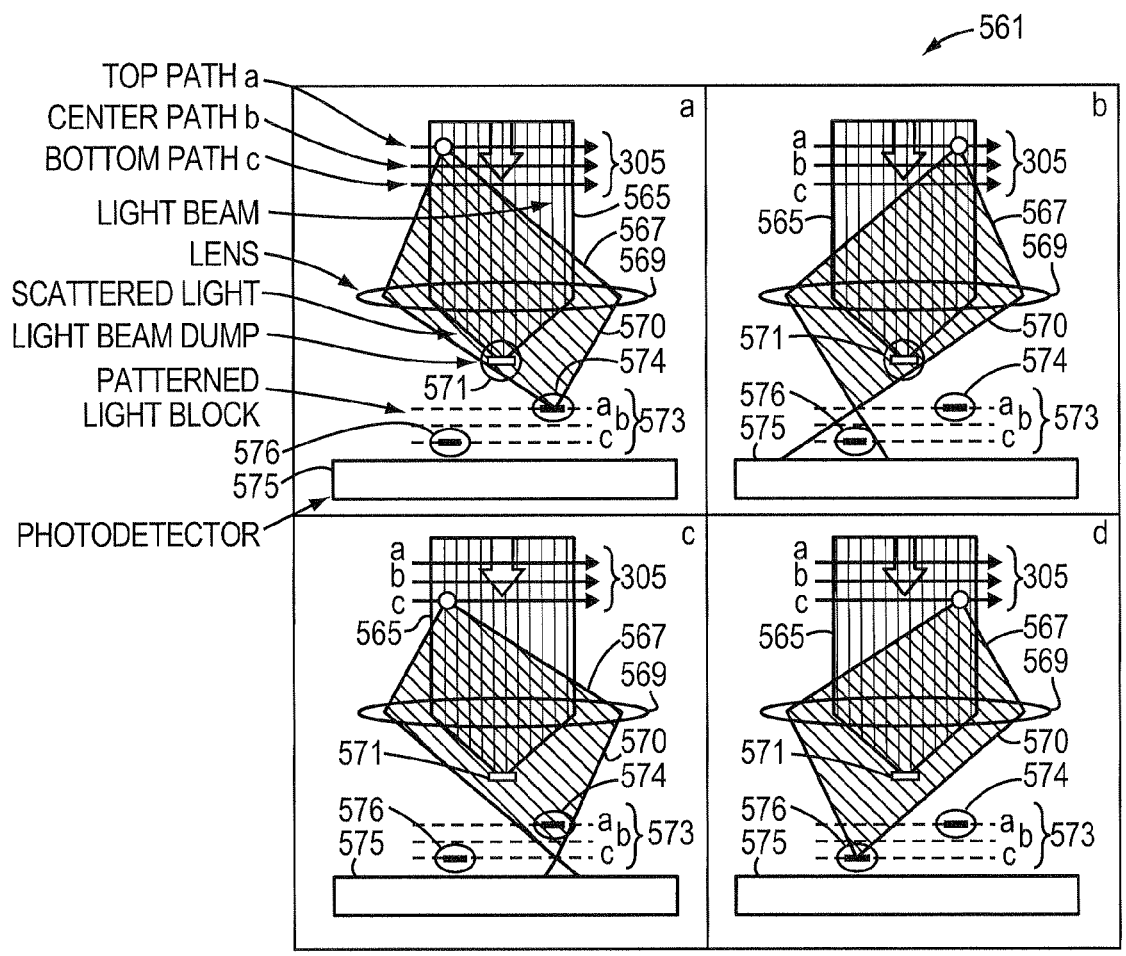
FIGS. 5C and 5D is a diagram of an alternative PSD system design and associated data signals, respectively, according to another embodiment of the present invention.

FIG. 5C provides illustrations of an alternative PSD system 561, examples a-d, that may provide a longitudinal particle position in a z, or first, dimension. In a first PSD 561, example a, an illumination beam 565 may be configured to travel in the z, or first, dimension. The illumination beam 565 may further be configured to intersect a sample volume 305 through which particles traveling in an x, or second, dimension travel. The particles may travel, for example, in a top path 305*a*, center path 305*b*, or bottom path 305*c*. The top, center, and bottom paths represent different positions of the particle in the z, or first, dimension.

As the particle travels in the x, or second, dimension and passes through the illumination beam 565, a diverging scattering light 567 may be produced. The diverging scattering light 567 may define a temporal profile that may, by the scattering, further include information indicative of the particle position in the z, or first, dimension. An optical focusing element 569 may be configured to focus the diverging scattering light 567, resulting in a converging scattering light 570. A light blocker 571 may be used to block the illumination beam 565, thus preventing a photodetector 575 from "seeing" the illumination beam 565, and, therefore, preventing detector saturation. The converging scattering light 570 may be focused onto a patterned optical block 573 placed in front of the detector 575. The optical block 573 may include three sections, for example, a top section 573*a*, center section 573*b*, and bottom section 573*c*. The top and bottom sections of the optical block 573*a*, 573*c* may use blocking sections 574 and 576, respectively, which may partially or completely block the scattering light 570 from reaching the light detector 575. Measuring a relative amount of light blocked by the blocking patterns 574 and 576, with respect to an amount of unblocked light, may provide information about where the particle is traveling in the z, or first, dimension.

Figure 5D:
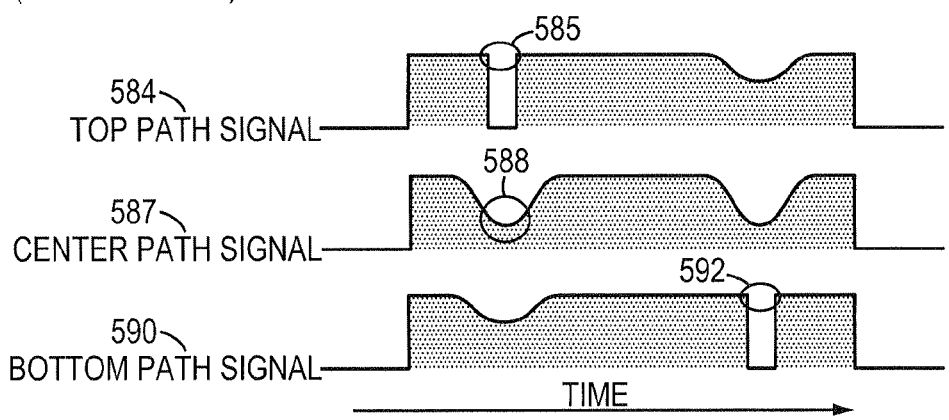

FIG. 5D provides an example of measured signals which may be obtained using the particle detection system 561. The top path signal 584 provides an example signal that may be obtained from a particle traveling along the top path 305a, as shown in the system in FIG. 5C. As shown in FIG. 5C, example a, a particle traveling along the top path 305a results in a converging scattering light 570 that is focused on the top layer of the optical block 573a, while the light scattering may be transmitted through the center and bottom layers of the optical beam block 573b and 573c, respectively. Therefore, the top path signal 584 includes a "total blocking" section 585, indicating that the particle has traveled along the top path 305a. If the particle has traveled only along the top path 305a, then only the top path signal 584 may include the total blocking portion 585. As illustrated in FIG. 5D, the center and bottom path signals 587 and 590, respectively, do not have a total blocking section 585 if the particle is traveling along the associated paths 305 b and 305 c respectively.

As also illustrated in FIGS. 5C and 5D, if a particle is traveling along the bottom path 305c of the sample volume 305, then only the bottom path signal 590 includes a total blocking portion 592. If the particle is traveling along the center path 305b of the sample volume 305, then neither the top nor bottom path signal 584, 590 has a total blocking portion. Based on the temporal profile of the signal (for example 584, 587, 590) a determination can be made as to which path (for example 305a-c) the particle traveled.

As is shown in FIG. 5C, example b, a particle traveling in the top portion, regardless of its position in the x, or second, dimension, may produce scattered light that only focuses on the top portion of the optical block 573a, this light being at least partially "transparent" to the middle and bottom portions of the optical block 573b and 573c, respectively. Similarly, as seen in the particle detection systems 561, example c, a particle traveling in the bottom path 305c of the sample volume 305 may produce a focused scattering light 570 that may only be focused on the bottom layer of the optical block 573c. Therefore, the produced scattered light 567 may be capable of being at least partially transmitted through the top and middle layers of the optical block 573a and 573b, respectively. As seen from the optical particle system 561, example d, the particle traveling in the bottom path, regardless of its position in the x, or second, dimension, is only focused on the bottom layer of the optical beam block 573.

It should be appreciated that the PSD systems of FIGS. 5C and 5D may be employed, provided that the first, second, and third dimensions are orthogonal to each other, in a preferred embodiment. It should also be appreciated that the PSD systems of FIGS. 5A and 5C may be used in conjunction with one another in order to determine the particle position in two dimensions, for instance in the example embodiments described above, a particle position may be found in the y and z dimension.

It should further be appreciated that the above described PSD systems are merely examples and that other forms of position sensitive detection may be employed to determine the position of particles within a sample volume. Other examples of PSD system may be found in U.S. application Ser. No. 11/804,593, which is incorporated by reference.

Another example of a PSD system may include an electrostatic measuring technique. Using an electrostatic measuring technique, the position of a particle may be determined by measuring the electric field disturbance caused by the particle in the sample volume. The electric field disturbance may be measured, for example, with the use of an array of capacitor plates or wires.

Figure 6:
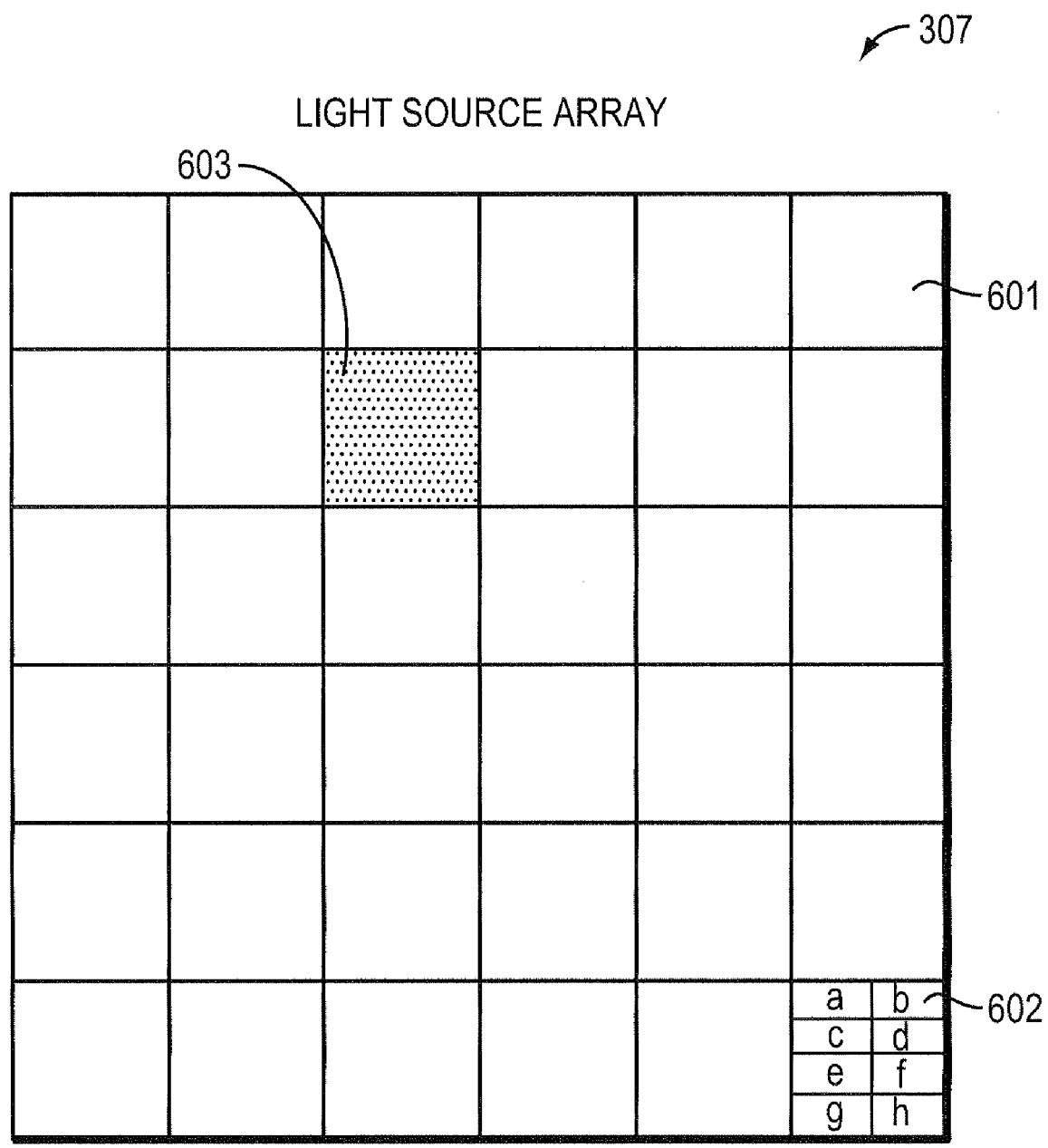
FIG. 6 is a schematic diagram of a smart pixel light source array according an embodiment of the present invention.

Light Source Arrays:

FIG. 6 is a schematic of a 6×6 light source array 307. Each individual box, such as box 601, represents a sub-element of the illumination array 307. The sub-element may be an individual LED, laser, or any other light source known in the art. Using the PSD system, the light source array 307 may illuminate specific portions of the sample volume 305 using any number of sub-elements at a time; for example, one pixel may be illuminated at a time as shown 603. In this embodiment, the individual sub-elements of the light source array may be individually and independently addressable so that any combinations of the sub-elements may be simultaneously or sequentially activated. Such a lighting system may be advantageous since, in an embodiment in which only a selected portion of pixels is illuminated, less power is required. Additionally, by activating only those light source sub-elements that illuminate particles in the sample volume, less light is transmitted to the sample volume than if all the sub-elements were activated. Transmitting less light into the sample volume reduces the amount of background photon noise, caused by either elastic scattering or luminescence of molecular vapors that fill the sample volume or by scattering or luminescence of physical structure near the sample volume.

Alternatively, each light source sub-element may be itself and array of smaller light source inner sub-elements 602, where each sub-element may comprise a plurality of light inner sub-elements 602a-h, each light source inner sub-element having a different wavelength. The plurality of light sources inner sub-elements 602a-h may be sequentially illuminated and used in the sequential illumination method discussed in relation to FIG. 3D.

Multiple light source arrays may be employed in the particle detection system. The multiple light source arrays may be used sequentially, wherein one light source array may illuminate the particle with light of one wavelength and, thereafter, another light source array may immediately illuminate the same particle with light of a different wavelength. Particles may exhibit different elastic scattering and luminescence properties when illuminated with light of different wavelengths. The use of multi-wavelength illumination may increase the number of useful measurements used in the discrimination and classification of particles. It should be appreciated that although FIG. 6 depicts the light pixel array as a 6×6 square grid, a light source grid comprising any shape or dimension may be employed.

Smart Binning:

Another advantage of the particle detection system presented herein is a "smart" binning technique employed by the detector array 319. Pixel binning is a reading process commonly used with CCDs.

Figure 7:
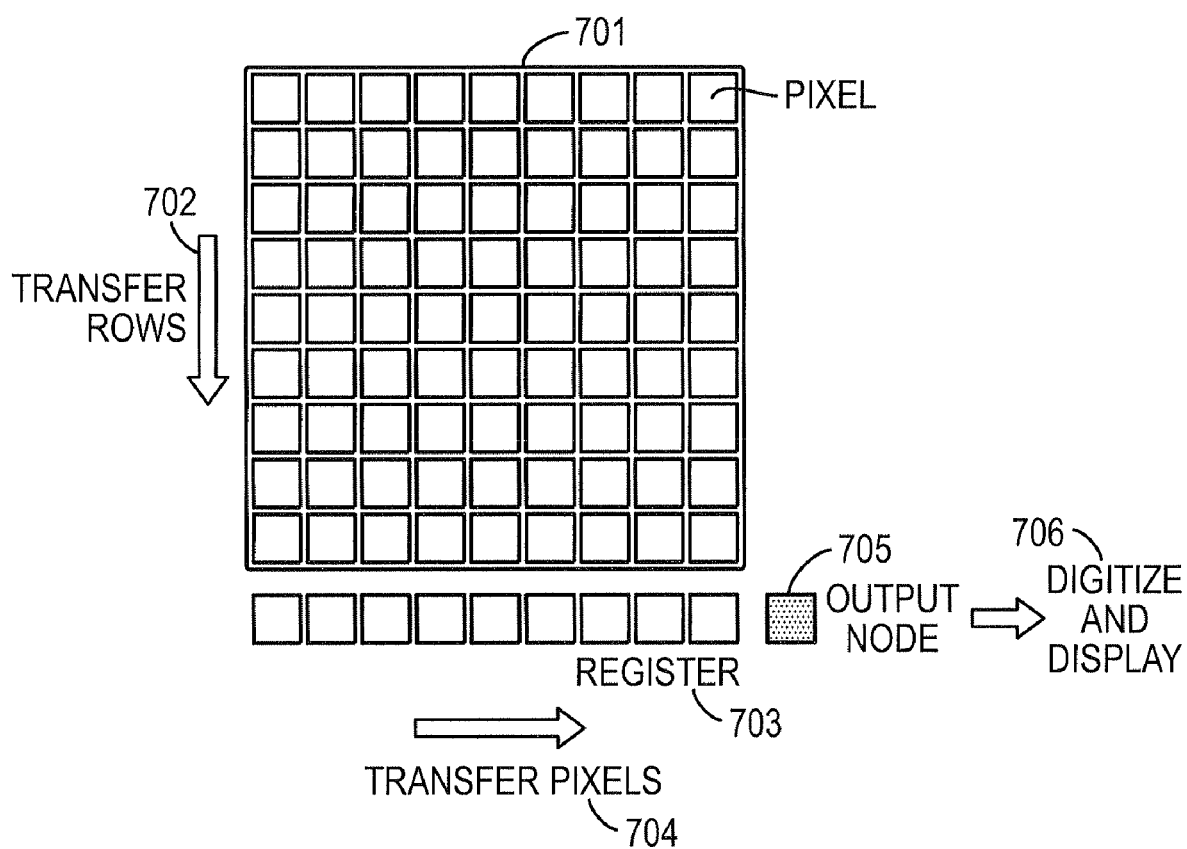
FIG. 7 is an illustrative example of charge coupled device (CCD) binning according to the prior art.

FIG. 7 provides an illustrative prior art example of CCD pixel binning. The CCD device 701 includes a plurality of individual detectors or pixels. Typically, a CCD is exposed to light, resulting in a charge build-up in the individual pixels proportional to the amount of light incident on the pixels. Typically the charge in the CCD pixels is read out by transferring the charge downward 702 in each pixel to a register 703 and then onto an output node 705 where the charge from each pixel is read out one pixel at a time. In this way an "image" of the light intensity on the CCD is obtained by digitizing and displaying the charge in each pixel 706.

An important consideration in using CCD detectors is the noise associated with these detectors. This noise consists of dark noise, or noise in each pixel which is not associated with light and read noise, or noise associated with the read out of each pixel. To compensate for the noise associated with the CCD detectors, a binning process may be employed. Binning is a process in which the charge in a group of adjacent pixels is transferred to a single output node 705 and digitized. Binning may be used to read out all or part of the CCD charge in either one or multiple read outs. Binning has the advantage of reducing the read noise associated with a group of pixels to that of a single pixel. Because the addition, or binning, of the charge on the CCD is very efficient and virtually noise free. In cases where loss of the image information within the binned area is acceptable, binning can reduce the overall noise of a measurement. This noise reduction allows the detection of weaker signals.

Typical applications of binning utilize predetermined and fixed locations and sizes of the group of pixels to be binned. In an application of binning for particle detection, as outlined here, the binning location and bin size may change from read out to read out because the position of particle signal changes from particle to particle and because separate measurements (e.g. particle size) may indicate utility in changing the binning size. This type of binning is referred to as smart binning.

In an embodiment of the present invention, particle position information from the PSD system may be used to determine what CCD locations to bin and the size of the binned regions may be determined by other particle measurements.

Figure 8:
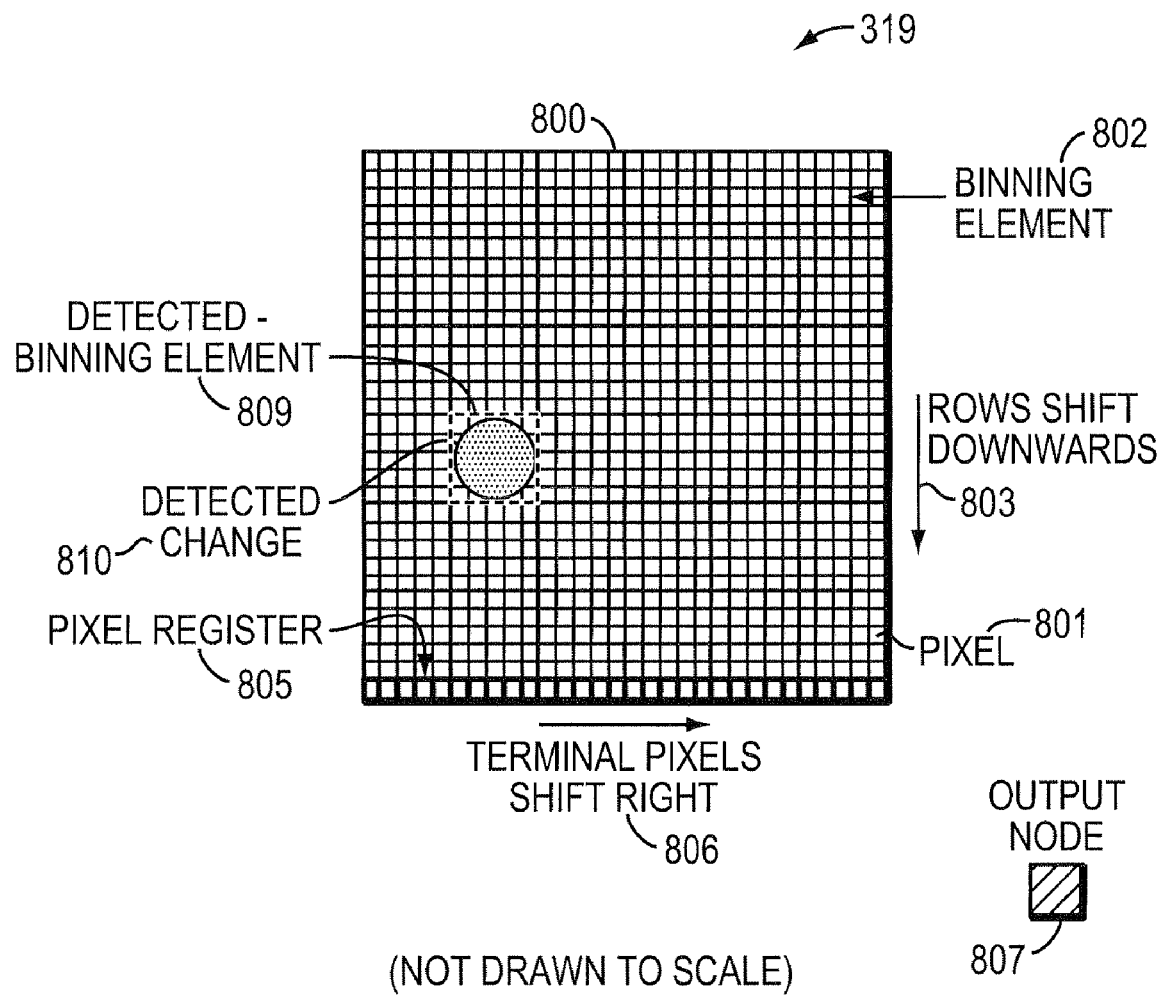
FIGS. 8 and 9A-9C are block diagrams of a pixel array detector with "smart" binning applied according to an embodiment of the present invention.

FIG. 8 is an example depiction of the detector array 319 of the particle detection system depicted in FIGS. 3A-3E. The detector array 319 may be in the form of a grid 800 including a plurality of individual detection pixels 801. In FIG. 8 a binning element 802 is composed of an array of detector sub-elements or pixels 801. In the example provided by FIG. 8, the binning element 802 includes a 5×5 square of pixels. The binning element 802 may define the grouping of individual pixels 801 that are shifted downward 803 onto the pixel register 805 and shifted to the output node 807. The binning element may then be read from the output node 807 in a single reading, or access. Using position information provided by the PSD system previously discussed, the binning elements 802 of the array detector 319 which contain particle light induced charge can be known. Furthermore, the position information provided by the PSD system may also be used to adjust the size of the binning elements 802. Thus, the PSD system allows dynamic binning adjustments through out detection process of particles.

For example, the PSD may provide location information indicating that a charge 810 from scattered light may be detected within a particular region of the detector grid 800. Upon a read command, a detected binning area 809 may be selected to enclose the detected charge 810 and shift the charge 810 downward 803, causing any charge in the detected binning area 809 to be transferred to a pixel register 805. The charge may then be horizontally transferred 806 onto an output node 807 for processing and digitizing the detected charge with a single read access.

Figure 9A:
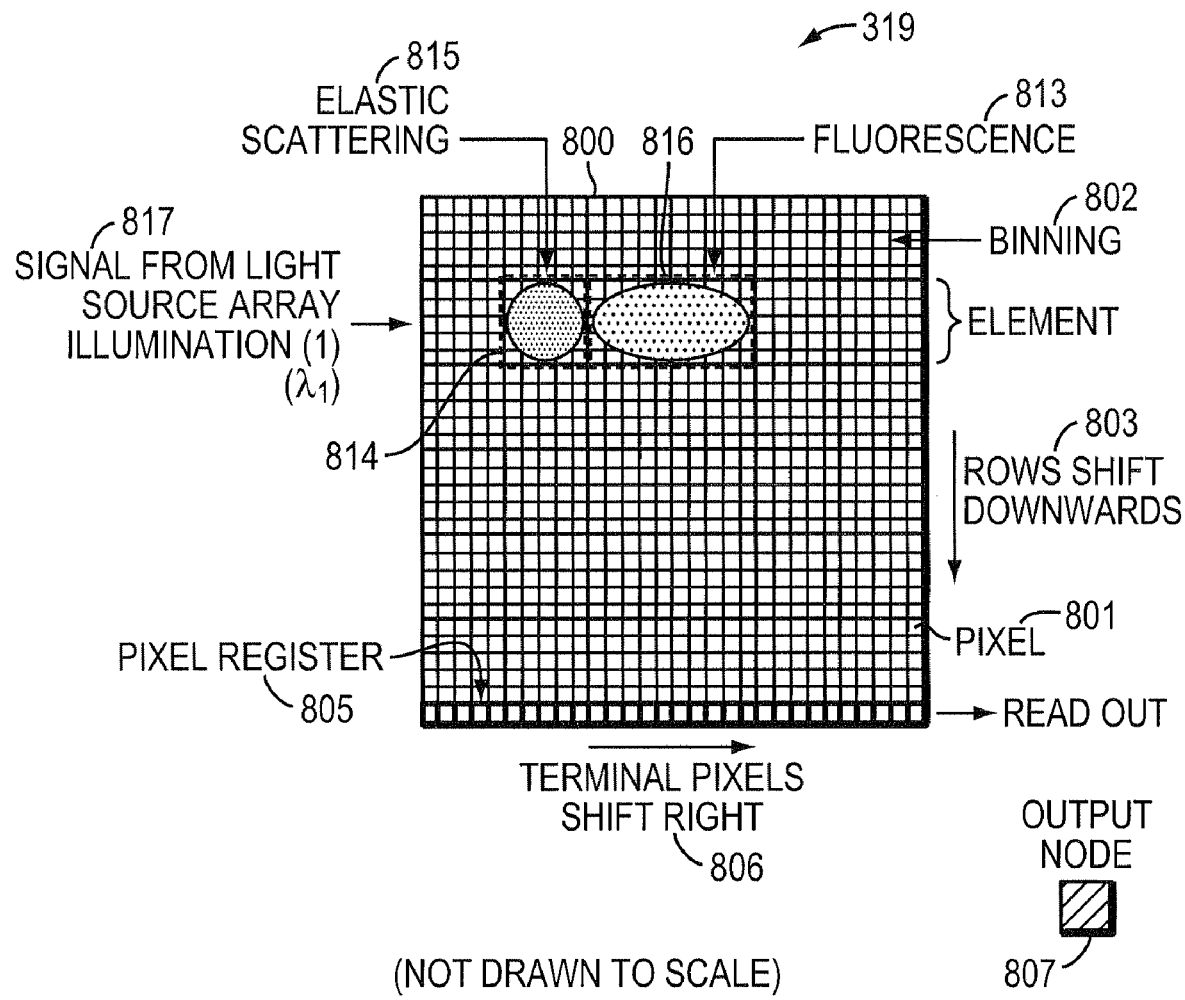
Figure 9B:
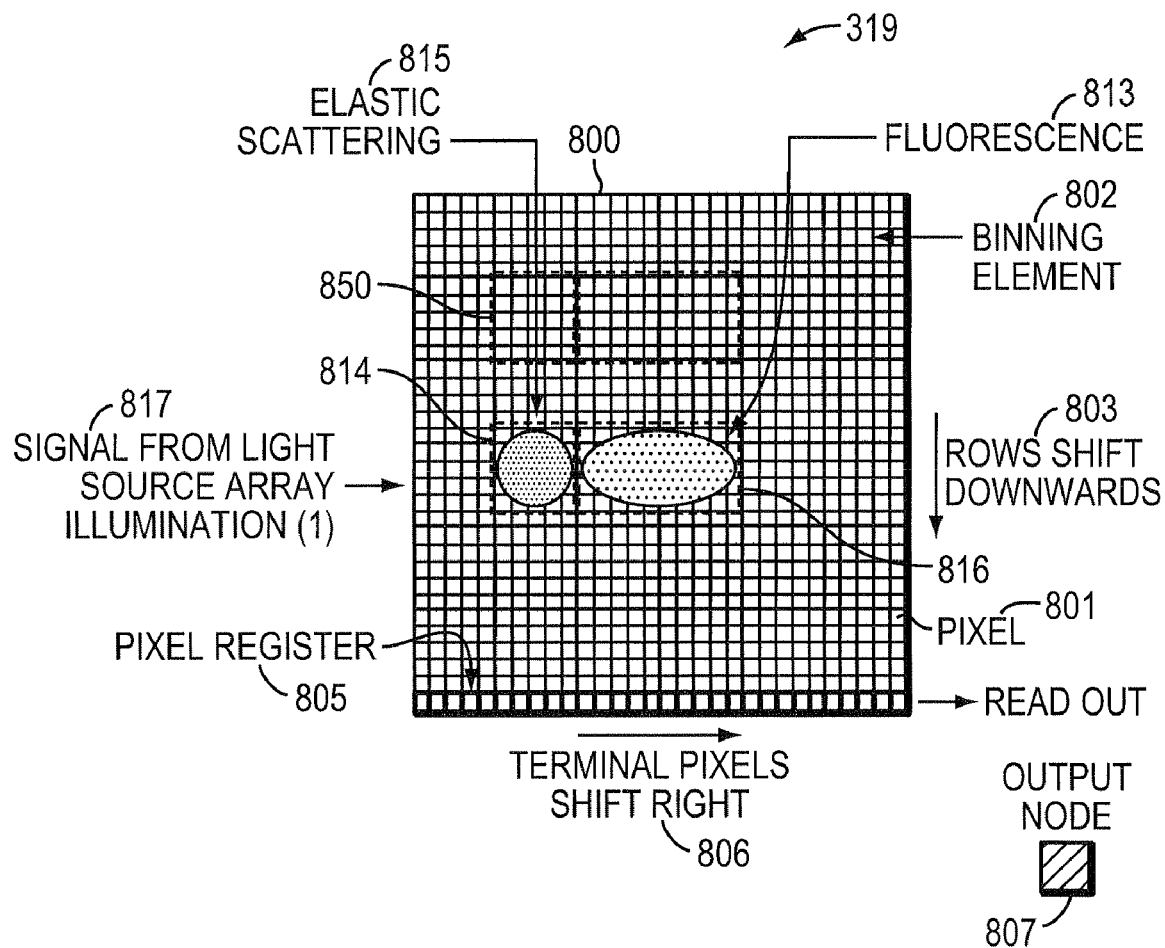
Figure 9C:
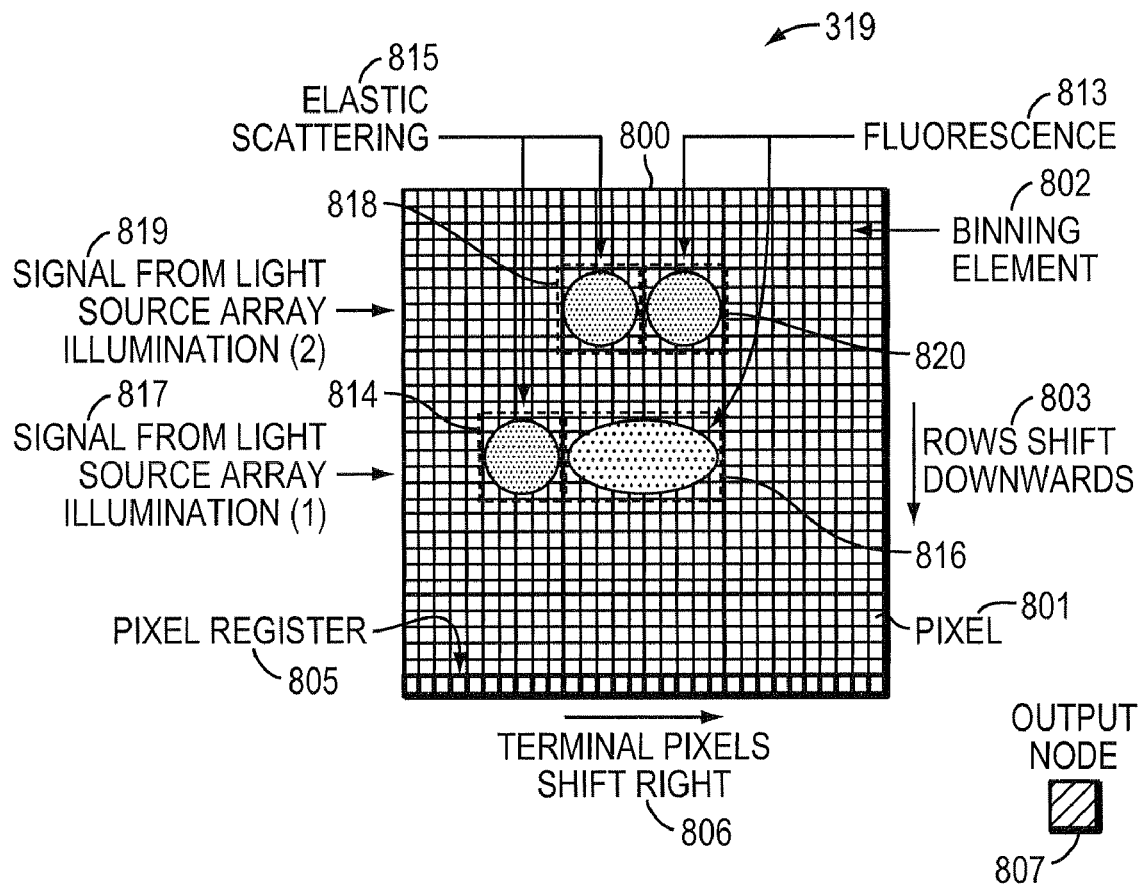

Particle discrimination may be further enhanced by sequentially illuminating the particle with different wavelength radiation while the particle is in the sample volume and separately recording on the detector array emission spectrum (e.g., elastic and/or luminescence scattering) from each illumination wavelength, as shown in FIGS. 9A-9C.

For example, consider a particle being illuminated with light of a first wavelength ($\lambda_1$) via a first light source array (1), as illustrated in FIG. 9A. The pixel array detector 319 stores the charge, or signal 817, generated from the particle illumination of the first light source array (1), on the grid 800 resulting from an elastic light scattering 815 and/or a luminescence or fluorescence light scattering 813. The luminescence or fluorescence signal is spanning a range of wavelengths, which may be provided by dispersing a particle light signal, as was discussed previously in relation to FIG. 3C. Employing particle location information from the PSD system, binning elements 814 and 816 may be defined for binning the elastic scattering and luminescence or fluorescence signals 815 and 813, respectively.

Because the particles travel along the optical axis of the detector imaging system, the image of the particle does not move on the detector. Rather, the size of the particle image changes depending upon whether the particle is in front of, behind or at focus of the detection system. Therefore, the signal 817 may be electronically shifted downward 803 in anticipation of a second illumination of the same particle so that the second signal does not overlap with the signal generated from the first light source array 817. The signal 817 may be shifted downward 803 with particle position information provided by the PSD system.

Thus, upon the particle illumination from the first light source array (1), the particle may be sequentially illuminated from a second light source array (2) illuminating with a second wavelength ($\lambda_2$). The particle is sequentially illuminated, as opposed to simultaneously illuminated, to avoid confusion of which part of the particle signal is due to which source beam. It should be noted that the size of the particle image may be minimized as the particle passes through the sample volume by only activating the light source when the particle is near the center of the sample volume.

FIG. 9B depicts the signal 817 having been shifted downward 803 from its previous position 850. The shifted signal may be placed in an area of the grid 800 unlikely to receive signal information, based on data from the PSD system. It should be appreciated that the charge may be shifted in any direction, for example upwards, to the left, or to the right. Immediately following the signal shifting, a second signal may be recorded.

FIG. 9C depicts a signal 819 resulting from an illumination of the particle via the second illumination pixel array (2) illuminating with light of a second wavelength ($\lambda_2$). Thus, two signals 817 and 819, each signal being the result of illumination from a different wavelength, ($\lambda_1$) and ($\lambda_2$) respectively, from the same particle, may be obtained. The signals defined by binning areas 814, 816, 818, and 820 may be binned separated in a manner allowing each defined binning area to be read from output node 807 with a single read access.

It should be appreciated that multiple signals, resulting from any number of light sources of any number of wavelengths, may be placed on the grid 800 at any one time. It should also be appreciated that any number of defined binning areas may be used to bin a signal. For example, the defined binning area 816 may be broken into two separate binning areas so that different portions of the particle emission spectrum may be recorded. The ability to simultaneously record multiple spectra from multiple particles and to reconfigure which portions of the spectra are read out is a great advantage that the array detector 319 possesses over prior art detection systems (e.g., PMT systems).

The many options available to binning the signal allow great flexibility in acquiring signals from different types of particles. In one embodiment, a binning scheme may be employed where all elastic scattering signals are captured in a single bin and fluorescence signals are captured into as many bins as desired. In another embodiment the image from the particles that generate large signals may be divided into many bins for enhanced spectral resolution while the image from particles that generate small signals may be binned into very few bins in order to achieve an adequate signal-to-noise ratio. The binning scheme employed for a particular reading may also be altered or updated for each individual reading and each individual particle.

It should be appreciated that other measurements may also be useful for determining the optimal binning regions for particle detection. For example, measurement of the amplitude, angular distribution or polarization of elastically scattered light may be used to infer the particle size, particle shape, absorption coefficient, and optical activity, which may help decide which particle signals should be read-out and how the binning of elastic scattering and fluorescence or luminescence scattering should be optimally configured. These decisions can be made in real time and individually for each particle.

The "smart" binning method may greatly improve throughput and efficiency of the detection system 201 (FIG. 2). For example, as a particle may be moving in a downward fashion through the fluid stream, the pixel detection array may dynamically bin received signals by optimizing the defined binning area in accordance with the movement of the particle through the sample volume.

It should also be appreciated that the "smart" binning method may be employed when the particles are imaged transversely on the detector array (e.g., when a particle is not traveling along the optical axis of the detector imagining system). In the case of traverse imagining, time delay and integration (TDI) may be used to shift the charge on the detector array at a same rate that the particle image travels across the detector array.

It should further be appreciated that the "smart" binning technique may be performed without the use of a PSD system. For example, the detector array may be configured to read-out the array uniformly until a significant charge is detected. This significant charge may be due to only part of the particle signal. Once an area including a significant charge is detected, the array may be dynamically binned in a manner that only the area including the remaining particle charge will be read out. In this way the remaining particle charge can be binned and read out with a low signal to noise ratio.

While this invention has been particularly shown and described with references to example embodiments thereof, it will be understood by those skilled in the art that various changes in form and details may be made therein without departing from the scope of the invention encompassed by the appended claims.

It should be understood that certain processes, such as smart binning, disclosed herein, may be implemented in hardware, firmware, or software. If implemented in software, the software may be stored on any form of computer readable medium, such as random access memory (RAM), read only memory (ROM), compact disk read only memory (CD-ROM), and so forth. In operation, a general purpose or application specific processor loads and executes the software in a manner well understood in the art.

What is claimed is:

1. A system for imaging particles a fluid flow, comprising:
    a light source to provide light to illuminate at least a portion of a sample volume through which particles flow to produce particle radiation caused by a particle being illuminated by the light;
    a position sensitive detector to provide a measured particle position of the particle in the sample volume;
    a detector array and optical system positioned to image the particle radiation at a substantially fixed location on the detector array; and
    a detector array controller to dynamically shift charge, produced by the particle radiation, on the detector array, based on the measured particle position, to image the particle radiation without overlap at the substantially fixed location.

2. The system of claim 1 further including a detector array read-out mechanism to bin the particle radiation that is incident on the detector array based on the measured particle position.

3. The system of claim 1 wherein the particle radiation includes elastically scattered light and luminescent light.

4. The system of claim 1 further including a processor coupled to the detector array to discriminate the particles from other particles in the sample volume based on measured particle radiation.

5. The system of claim 4 wherein the processor is configured to detect elastically scattered light and at least a portion of luminescent light at different wavelengths.

6. The system of claim 4 further including a database configured to be used by the processor to store signals representative of different particles in the fluid flow.

7. The system of claim 4 wherein the processor is configured to generate a signal to notify the user of the presence of a particle that normally does not flow through the sample volume.

8. The system of claim 1 wherein the light source is a multiple wavelength light source configured to have wavelengths selectively activated.

9. The system of claim 1 wherein the light source comprises an array of light emitters, the light emitters configured to be selectively activated to illuminate respective portions of the sample volume at which the particle is located as determined the measured particle position.

10. The system of claim 1 wherein the detector array includes a Charge Coupled Device (CCD) array to image the particle radiation.

11. The system of claim 1 wherein the detector array includes a Geiger-mode avalanche photodiode (GM-APD) array to image the particle radiation.

12. The system of claim 1 further including an optical assembly to direct the particle radiation toward the detection array substantially free from illuminating the detector array with light from the light source.

13. The system of claim 1 wherein the position sensitive detector is configured to measure the particle position based on the particle radiation.

14. The system of claim 1 wherein the position sensitive detector is configured to measure the particle position based on an electric field disturbance caused by the particle in the sample volume.

15. The system of claim 1 further including an optical assembly to longitudinally image the particle radiation on the detection array.

16. The system of claim 1 further including an optical assembly to transversely image the particle radiation on the detector array and the system further including a time delay and integration (TDI) sub-system to dynamically shift and bin the particle radiation according to the measured particle speed and position.

17. A method of imaging particles, comprising:
    illuminating, with a light source, at least a portion of a sample volume through which particles flow;
    measuring a particle position of a particle in the sample volume;
    imaging particle radiation produced by the particle being illuminated by lights from the light source at a substantially fixed location on a detector array; and dynamically shifting charge, produced by the particle radiation, on the detector array, based on the measured particle position, to image the particle radiation without overlap at the substantially fixed location.

18. The method of claim 17 further including dynamically binning the particle radiation that is incident on the detector array based on the measured particle position.

19. The method of claim 17 wherein imaging the particle radiation further comprises imaging elastically scattered light and luminescent light.

20. The method of claim 17 wherein imaging the particle radiation further comprises discriminating the particles from other particles in the sample volume based on measured particle radiation.

21. The method of claim 20 wherein discriminating the particles further comprises detecting elastically scattered light and at least a portion of luminescent light at different wavelengths.

22. The method of claim 20 wherein discriminating the particles further comprises storing signals representative of different particles in the particle flow.

23. The method of claim 17 wherein illuminating with the light source further comprises selectively activating wavelengths of a multiple wavelength light source.

24. The method of claim 17 wherein illuminating with the light source further comprises selectively activating light emitters, from an array of light emitters, to illuminate a portion of the sample volume at which the particle is located based on the measured particle position.

25. The method of claim 17 wherein imaging the particle radiation includes operating a Charge Coupled Device (CCD).

26. The method of claim 17 wherein imaging the particle radiation includes operating a Geiger-mode avalanche photodiode (GM-APD) array.

27. The method of claim 17 further comprising directing the particle radiation toward the pixel based array substantially free from illuminating the detector array with light from the light source.

28. The method of claim 17 wherein measuring the position of the particle in the sample volume is based on the particle radiation.

29. The method of claim 17 wherein measuring the position of the particle in the sample volume is based on an electric field disturbance caused by the particle in the sample volume.

30. The method of claim 17 wherein imaging the particle radiation is performed longitudinally.

31. The method of claim 17 wherein imagining the particle radiation is performed transversely and the dynamic shifting is performed with the use of a time delay and integration (TDI) sub-system.

32. A system for imaging particles a fluid flow, comprising:
means for illuminating at least a portion of a sample volume through which particles flow to produce particle radiation caused by a particle;
means for measuring a particle position of the particle in the sample volume;
means for imaging the particle radiation at a substantially fixed location; and
means for shifting charge, produced by the particle radiation, based on the measured particle position, to image the particle radiation without overlap at the substantially fixed location.

* * * * *